(12) United States Patent
Lin et al.

(10) Patent No.: US 6,878,838 B2
(45) Date of Patent: Apr. 12, 2005

(54) CHIRAL POROUS METAL PHOSPHONATES FOR HETEROGENEOUS ASYMMETRIC CATALYSIS

(75) Inventors: Wenbin Lin, Chapel Hill, NC (US); Aiguo Hu, Chapel Hill, NC (US); Helen L. Ngo, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 32 days.

(21) Appl. No.: 10/395,375

(22) Filed: Mar. 24, 2003

(65) Prior Publication Data

US 2004/0192543 A1 Sep. 30, 2004

(51) Int. Cl.$^7$ .......................... C07F 19/00; B01J 31/00; C07C 29/14

(52) U.S. Cl. .......................... 556/14; 556/28; 502/162; 502/166; 568/862

(58) Field of Search .................... 556/14, 28; 568/862; 502/162, 166

(56) References Cited

U.S. PATENT DOCUMENTS

| 4,384,981 | A | 5/1983 | Dines et al. |
| 4,386,013 | A | 5/1983 | Callahan et al. |
| 6,508,753 | B2 | 1/2003 | Burk et al. |
| 6,515,156 | B2 | 2/2003 | Kenzo et al. |
| 6,521,769 | B1 | 2/2003 | Zhang |
| 6,528,687 | B2 | 3/2003 | Cobley et al. |

FOREIGN PATENT DOCUMENTS

| EP | 1 254 885 | 11/2002 |

OTHER PUBLICATIONS

Köckritz et al., Journal of Molecular Catalysis A: Chemical 174 (2001) 119–126.*
Alberti, G., et al., "Zirconium Phosphite (e,3',5,5'–Tetramethyl–biphenyl)diphosphonate, a Microporous, Layered, Inorganic–Organic Polymer**", *Angew. Chem., Int. Ed. Engl.*, 32(9): 1357–1359, 1993.
Boaz, N.W., et al., "Phosphinoferrocenylaminophosphines as Novel and Practical Lignands for Asymmeric Catalysis", *Org. Lett.*, 4(14): 2421–2424, 2002.
Clearfield, A. and Wang, Z., et al., "Organically pillared microporous zicronium Phosphanes",*J. Chem.. Soc., Dalton Trans:* 2937–2947, 2002.
Clearfield, A., "Metal Phosphonate Chemistry" *Progress in Inorganic Chemistry,* (John Wiley & Sons, Inc.) 47: 371–510, 1998.
Cui, Y., et al., "Rational Design of Homochiral Solids Based on Two–Dimensional Metal Carboxylates**", *Angew. Chem., Int. Ed.,* 41(7): 1159–1161, 2002.

Doucet, H., et al., "trans–[RuCl$_2$)phosphane)$_2$(1,2–diamine)] and Chiral trans–[RuCl$_2$(diphosphane)(1,2–diamine): Shelf–Stable Precatalysts for the Rapid, productie, and Stereoselective Hydrogenation of Ketones** ", *Angew. Chem. Int. Ed.,* 37(12): 1703, 1998.
Eddaoudi, D. B., et al., "Modular Chemistry: Secondary Building Units as a Basis for the Design of Highly Porous and Robust Metal–Organic Carboxylate Frameworks", *Acc. Chem. Res.,* 34(4): 319–330, 2001.
Evans, O. R., et al., "Crystal Engineering of NLO Materials Based on Metal–Organic Coordination Networks", *Acc. Chem. Res.,* 35(7): 511–522, 2002.
Evans, O. R., et al., "Chiral Porous Solids Based on Lamellar Lanthanide Phosphonates", *J. Am. Chem. Soc.,* 123(42): 10395–10396, 2001.
Fan, Q. H., et al., "Recoverable Catalysts for Asymmetric Organic Synthesis", *Chem. Rev.,* 102(10): 3385–3465, 2002.
Hagrman, P. L., et al., Organic–Inorganic Hybrid Materials: From "Simple" coorgination polymers to Organodiamine–Templated Molybdenum Oxides, *Angew. Chem., Int. Ed.,* 38: 2638–2684, 1999.
Inagaki, S., et al., "An ordered mesoporous organosilica hybrid material with a crystal–like wall structure", *Nature,* 416: 304–307, 2002.
Ireland, T., et al., "Synthesis of a New Class of chiral 1,5–Diphosphanylferrocene Ligands and Their Use in Enantioselective Hydrogenation", *Chem. Eur. J.,* 8(4): 843–852, 2002.
Janiak, C., "Functional Organic Analogues of Zeolites based on metal—Organic Coordination Frameworks**", *Angew. Chem., Int. EngL. Ed.:* 36(13 & 14): 1431–1434, 2002.
Kant., M., et al., "Synthesis and Characterization of 4– and 4,4'–Phosphorylated 2,2'–Bis(diphenylphosphanyl)–1,1'–binaphthyls", *Eur. J. Org. Chem.,* 477–481, 2001.

(Continued)

*Primary Examiner*—Porfirio Nazario-Gonzalez
(74) *Attorney, Agent, or Firm*—Jenkins, Wilson & Taylor, P.A.

(57) ABSTRACT

Chiral porous zirconium phosphonates containing metal complex moieties are provided, synthesized via a molecular building block approach, and characterized by a variety of techniques including TGA, adsorption isotherms, XRD, SEM, IR, and microanalysis. These hybrid solids may be used for enantioselective heterogeneous asymmetric hydrogenation of aromatic ketones with remarkably high e.e. values of up to 99.2%. Similarly prepared chiral porous solids may be used for asymmetric hydrogenation of β-keto esters with e.e.'s of up to 95%. The solid catalysts can also be easily recycled and reused multiple times without the loss of activity and enantioselectivity. Ready tunability of such a molecular building block approach allows the optimization of these hybrid materials to provide practically useful heterogeneous asymmetric catalysts.

35 Claims, 23 Drawing Sheets

OTHER PUBLICATIONS

Kapoor, M.P., et al., "Self–Assembly of Biphenylene–Bridged Hybird Mesoporous Solid with Molecular–Scale Periodicity in the Pore Walls", *J. Am. Chem. Soc.*, 124(51): 15176–15177, 2002.

Kitamura, M., et al., "Homogeneous Asymmetric hydrogenation of Functionalized Ketones", *J. Am. Chem. Soc.*, 110: 629–631, 1988.

Knowles, W. S., "Asymmetric Hydrogenations (Novel Lecture 2001)", *Adv. Synth. Catal.*, 345: 3–13, 2003.

Mallouk, T. E. and Gavin, J. A., "Molecular Recognition in Lamellar Solids and Thin Films", *Acc. Chem. Res.*, 31(5): 209–217, 1998.

Matsumoto, T., et al. "Diastereoselective Synthesis of a Key Intermediate for the Preparation of Tricyclic β–Lactam Antibiotics", *Tetra. Lett.*, 40: 5043–5046, 1999.

Moulton, B. and Zawarotko, M., "From Molecules to Crystal Engineeering: Supramolecular Isomerism and Polymorphism in Network Solids", *Chem. Rev.*, 101(6): 1629–1658, 2001.

Ngo, H. L., and Lin, W., "Chiral Crown Ether Pillared Lamellar Lanthanide Phosphonates", *J. Am. Chem. Soc.*, 124: 14298–14299, 2002.

Noyari, R., "Asymmetric Catalysis: Science and Opportunities (Novel Lecture**", *Angew. Chem., Int. Ed.,*:41: 2008–2022, 2002.

Noyori, R., "BINAP: An Efficient Chiral Element for Asymmetric Catalysis", *Acc. Chem. Res.*, 23: 345–350, 1990.

Ohkuma T., et al., "trans–RuH($\eta^1$–BH$_4$)(binap)1,2–diamine): A catalyst for Asymmetric Hydrogenation of Simple Ketones Under Base–Free Conditions", *J. Am. Chem. Soc.*, 124(23): 6508–6509, 2002.

Ohkuma, T., et al., "Asymmetric Hydrogenation of Amino Ketones Using Chiral RuCl$_2$(diphophine)1,2–diamine) Complexes", *J. Am. Chem. Soc.*, 122(27): 6510–6511, 2000.

Ohkuma, T., et al., "Asymmetric Hydrogenation of Alkenyl, Cyclopropyl, and Aryl Ketones, RUCl$_2$(xylbinap)(1,2–diamine) as a Precatalyst Exhibiting a Wide Scope", *J. Am. Chem. Soc.*, 120(51): 13529–13530, 1998.

Ohkuma, T., et al., "Preferential hydrogenation of Aldehydes and Ketones", *J. Am. Chem. Soc.*, 117(41): 10417–10418, 1995.

Park, J. K., et al., "Heterogeneous asymmetric Diels–Alder reactions using a copper–chiral bis(oxazoline) complex immobilized on mesoporous silica", *Tetrahedron: Asymmetry*, 12: 2931–2935, (Elsevier Science Ltd.) 2001.

Pu, L., "1,1'–Binaphthyl Dimers, Oligomers, and Polymers: Molecular Recognition, Asymmetric Catalysis and New Materials †", *Chem. Rev.*, 98(7): 2405–2094, 1998.

Saluzzo, C., and Lemaire, M., "Homogenious–Supported Catalysts for Enantioselective Hydrogenation and Hydrogen Transfer Reduction", *Adv. Synth. Catal.*, 344(10): 915–928, 2002.

Seo, J. S., et al., A Homochiral Metal–Organic Porous Material for Enantioselective Separation and Catalysis *Nature*, 404:982–986, 2000.

Sinou, D., "Asymmetric Organometallic–Catalyzed Reactions in Aqueous Media", *Adv. Synth. Catal.*, 344(3 & 4): 221–237, 2002.

Song, C. E., et al., "Supported Chiral Catalysts on Inorganic Materials" *Chem. Rev.*, 102(10): 3495–3524, 2002.

Yu, H. B., et al., "Synthesis of a rigid and optically active oly(BINAP) and its application in asymmetric catalysis", *Tetra. Lett.*, 41: 1681–1685, 2000.

Zhang, Z., et al., "Synthesis of chiral Bisphosphines with Turnable Bite Angles and Their Applications in Asymmetric Hydrogenation of β–Ketoesters", *J. Org. Chem.*, 65(19): 6223–6226, 2000.

Zhou, Y.–G., et al., "Highly Effective chiral Ortho–Substituted BINAPO Lignands (oBINAPO): Applications in Ru–Catalyzed Asymmetric Hydrogenations of β–(Acylamino) acrylates and β–Keto Esters", *J. Am. Chem. Soc.*, 124(18): 4952–4953, 2002.

* cited by examiner

SEM micrograph of Zr-Ru-L₂ solid precatalyst

TGA Curves of Zr-Ru-L$_1$ and Zr-Ru-L$_2$

Microporous BET plot for Zr-Ru-L$_1$

BET plot for Zr-Ru-L$_2$

Microporous BET plot for Zr-Ru-L$_2$

FT-IR spectrum of Ru(L$_1$-H$_4$)(DMF)$_2$Cl$_2$.

FT-IR spectrum of Zr-Ru-$L_1$.

FT-IR spectrum of Ru(L$_2$-H$_4$)(DMF)$_2$Cl$_2$.

FT-IR spectrum of Zr-Ru-$L_2$.

N₂ adsorption isotherms for Zr-Ru-$L_1$ and Zr-Ru-$L_2$ at 77 K. The inset shows BET plot for Zr-Ru-$L_1$ in the mesoporous region.

SEM image of the Zr-Ru-L$_1$ solid precatalyst

SEM micrograph of Zr-Ru-L$_2$-DPEN catalyst

SEM micrograph of Zr-Ru-L$_1$-DPEN catalyst

TGA Curves of Zr-Ru-L$_1$-DPEN and Zr-Ru-L$_2$-DPEN

Microporous BET plot for Zr-Ru-L$_2$-DPEN

BET plot for Zr-Ru-L$_1$-DEPN

Microporous BET plot for Zr-Ru-L$_1$-DPEN

FT-IR spectrum of Ru(L$_2$-H$_4$)(DPEN)Cl$_2$

FT-IR spectrum of Zr-Ru-$L_2$-DPEN

FT-IR spectrum of Ru(L$_1$-H$_4$)(DPEN)Cl$_2$

FT-IR spectrum of Zr-Ru-L₁-DPEN $N_2$ adsorption isotherms for Zr-Ru-$L_1$-DPEN and Zr-Ru-$L_2$-DPEN at 77 K.

Comparison between solid catalysts and Ru-BINAP-based homogeneous catalyst

CHIRAL POROUS METAL PHOSPHONATES FOR HETEROGENEOUS ASYMMETRIC CATALYSIS

This invention was made with Government support under Contract No. CHE-0208930 from the National Science Foundation. The Government may have certain rights to this invention.

BACKGROUND OF THE INVENTION

1. Field of the Invention

The present invention relates to chiral porous metal phosphonates synthesized via a molecular building block approach. The chiral porous metal phosphonates may function as catalysts for enantioselective heterogeneous asymmetric reactions such as asymmetric hydrogenation of a variety of prochiral substrates including alpha- and beta-keto esters, diketones, hydroxy ketones, simple ketones, enamides, and acrylic acid derivatives.

2. Description of Related Art

Asymmetric reduction of prochiral olefins, ketones and imines is a powerful method for the production of optically active compounds. For example, catalytic asymmetric hydrogenation is one of the most efficient strategies for the synthesis of optically active molecules. In particular, ruthenium and rhodium complexes of chiral chelating bisphosphines such as the Ru and Rh complexes of 2,2'-bis(diphenylphosphino)-1,1'-binaphthyl (BINAP) have been used for the reduction of a wide range of substrates including keto esters, alkenes, and ketones with high enantioselectivity. See, for example, *Angew. Chem., Int. Ed.* 2002, 41, 2008; *J. Am. Chem. Soc.* 2002, 124, 4952; *Acc. Chem. Res.* 1990, 23, 345. *J. Am. Chem. Soc.* 1988, 110, 629; EP 1 254 885. *J. Am. Chem. Soc.* 1995, 117, 10417; *Angew. Chem. Int. Ed.* 1998, 37, 1703; *J. Am. Chem. Soc.* 2000, 122, 6510; *J. Am. Chem. Soc.* 1998, 120, 13529; *J. Am. Chem. Soc.* 2002, 124, 6508. However, these complexes suffer from a number of disadvantages such as the high costs of both noble metals and chiral ligands and the necessity and difficulty in removing trace amounts of metals from the organic products. These disadvantages have hindered the application of homogeneous catalysts in many industrial processes.

Various methods of providing improved catalysts have been attempted. One of these methods is the heterogenization of homogeneous asymmetric catalysts as described in *Chem. Rev.* 2002, 102, 3385. Heterogenized catalysts may combine advantages of homogeneous and heterogeneous systems and provide solutions to both recycling and reusing expensive catalysts and preventing the leaching of metals. To date, several approaches have been used to heterogenize homogeneous asymmetric catalysts including attachment to porous inorganic oxide and insoluble organic polymer supports, incorporation into soluble organic macromolecules and membranes, and immobilization via biphasic systems.

For application in industrial asymmetric catalysis, however, an asymmetric hydrogenation or other catalyst needs to exhibit high activity and enantioselectivity in the desired transformation of a particular substrate. It is also important that the chiral ligand precursor can be prepared efficiently by a synthetic route that is amendable to scale-up. The heterogenized catalysts afforded by the previous methods, however, do not meet these requirements and are typically less effective than their homogeneous counterparts.

Thus, there is still a need in the art for effective heterogeneous asymmetric catalysts, methods of making such catalysts and methods of using heterogeneous asymmetric catalysts for a variety of asymmetric reactions. The present invention provides such heterogeneous asymmetric catalysts and methods.

BRIEF SUMMARY OF THE INVENTION

The invention provides chiral catalysts useful in asymmetric reactions. In particular, the invention provides methods for the synthesis and use of novel chiral porous hybrid solids as catalysts in heterogeneous asymmetric reactions. In one aspect, the chiral porous hybrid solids are metal phosphonates which combine a metal phosphonate framework with highly enantioselective metal complexes containing a chiral bisphosphine moiety. Preferably, the metal complexes contain a pendant chiral bisphosphine moiety and a diamine moiety.

In another aspect of the invention, chiral porous metal phosphonates are provided according to Formula I:

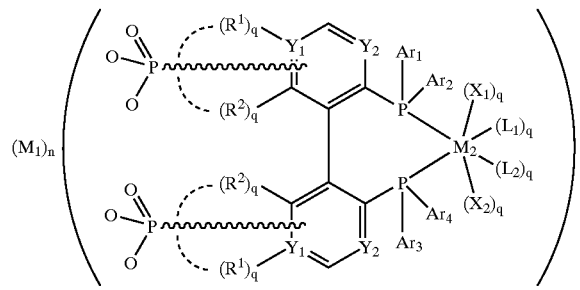

Formula I wherein $M_1$ is a group IV metal, a lanthanide metal, or any other first-row transition metal atom, n=1–2 and is a quantity such that Formula I retains charge neutrality regardless of the $M_1$ atom used; (by way of example, n is 1 when $M_1$ is a group IV metal atom);

$M_2$ is Ru, Rh, Ir, Os, Pt or Pd;

$X_1$ and $X_2$ may be covalently or ionically bonded to the $M_2$ center, and may each independently represent an anionic radical, preferably hydrogen, halogen, an alkoxy group, or a carboxyl group, but may be another anionic radical, by way of example, such as $BF_4^-$, $PF_6^-$, $AsF_6^-$ and the like;

$Ar_1$, $Ar_2$, $Ar_3$ and $Ar_4$ independently represent a phenyl group substituted with from zero to five substituents selected from straight-chain or branched-chain lower alkyl groups, halogen, or lower alkoxy groups;

$L_1$ and $L_2$ independently represent a coordinated solvent molecule, such as DMF, or $L_1$ and $L_2$ represent donor atoms comprising half of a diamine moiety such that $L_1$ and $L_2$ are joined to give a chelating diamine, or $L_1$ and $L_2$ represent a weakly coordinating ligand, such as an olefin, by way of example, $L_1$ and $L_2$ together may represent cyclooctadiene or norbornene;

$Y_1$ and $Y_2$ independently represent a carbon or nitrogen atom;

$R^1$ and $R^2$ independently represent hydrogen, a lower alkyl group, or a lower alkoxy group, or each pair of $R^1$ and $R^2$ can be the same or different and are bonded such that each $R^1$ and $R^2$ together with the attached ring form a ring selected from a substituted or unsubstituted tetrahydronaphthalene (by way of example, Tetralin™), a substituted or unsubstituted naphthalene ring, or a substituted or unsubstituted 1,3-benzodioxole ring, provided, however, that when $Y_1$ is N, $R^1$ is nothing;

P∼∼∼ represents a bond independently linking each of the phosphonate groups to the benzene, pyridine or pyrimidine ring or a ring formed by each of $R^1$ and $R^2$ as defined above, in any of the reasonable positions (by way of example, such as 3,3'-, 4,4'-, 5,5'-, or 6,6-') either directly or through one of the following linkages:

an alkene group, an alkyl group, an aryl group or a styryl group; and each q is independently selected from 0 or 1.

In one aspect, the chiral porous metal phosphonates are prepared by reacting a metal source with a phosphonic acid derivative of a homogeneous asymmetric catalyst comprising a metal complex containing a chiral bisphosphine moiety. The chiral porous metal phosphonates may function as asymmetric heterogeneous catalysts. In a preferred aspect, the metal complex further contains a diamine moiety and the metal source is a metal alkoxide or a metal halide, more preferably, metal alkoxide.

In another aspect of the invention, a method is provided for preparing a chiral porous metal phosphonate by first preparing a phosphonic acid derivative of a homogeneous asymmetric catalyst and then reacting the phosphonic acid derivative with a metal source to obtain the chiral porous metal phosphonate. The chiral porous metal phosphonates may function as asymmetric heterogeneous catalysts. In a related aspect, the homogeneous asymmetric catalyst contains a chiral bisphosphine moiety. In a preferred aspect, the homogeneous asymmetric catalyst further contains a diamine moiety and the metal source is a metal alkoxide or metal halide.

In a further aspect of the invention, a method is provided for preparing an asymmetric compound comprising contacting a substrate capable of forming an asymmetric product by an asymmetric reaction with a chiral porous metal phosphonate comprising the reaction product of a metal source and a phosphonic acid derivative of a homogeneous asymmetric catalyst.

In another aspect of the invention, a method is provided for the stereoselective hydrogenation of a substrate capable of forming an asymmetric product by hydrogenation comprising contacting the substrate with a chiral porous metal phosphonate comprising the reaction product of a metal alkoxide or a metal halide and a phosphonic acid derivative of a homogeneous asymmetric catalyst.

DETAILED DESCRIPTION OF THE INVENTION

Figure 1:
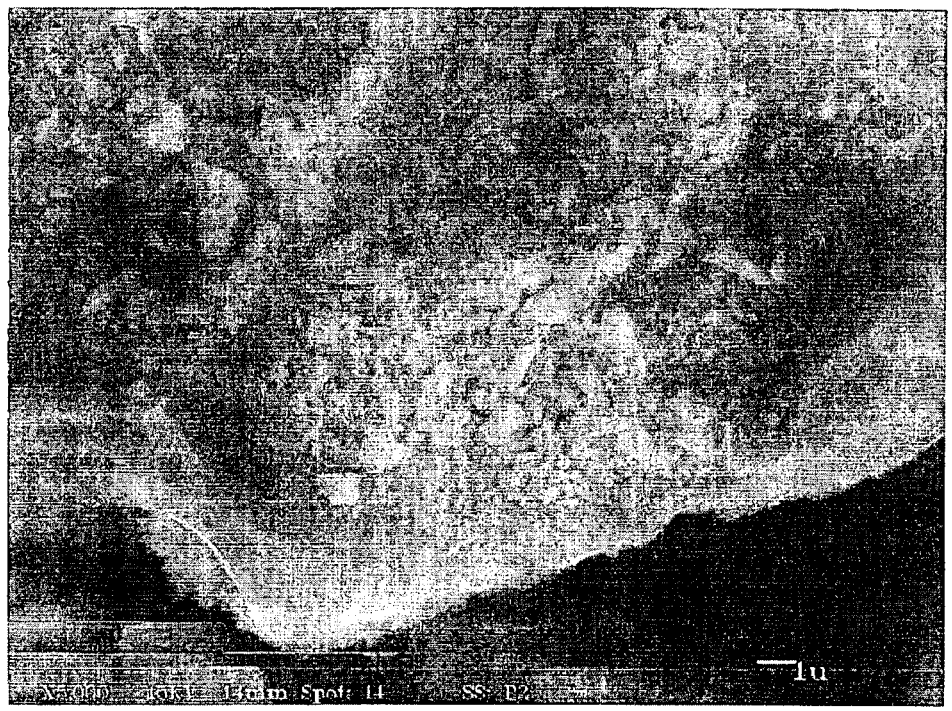
FIG. 1 is a scanning electron micrograph (SEM) of Zr—Ru—$L_2$ as obtained by the experimental procedures described in Example 1.
Figure 2:
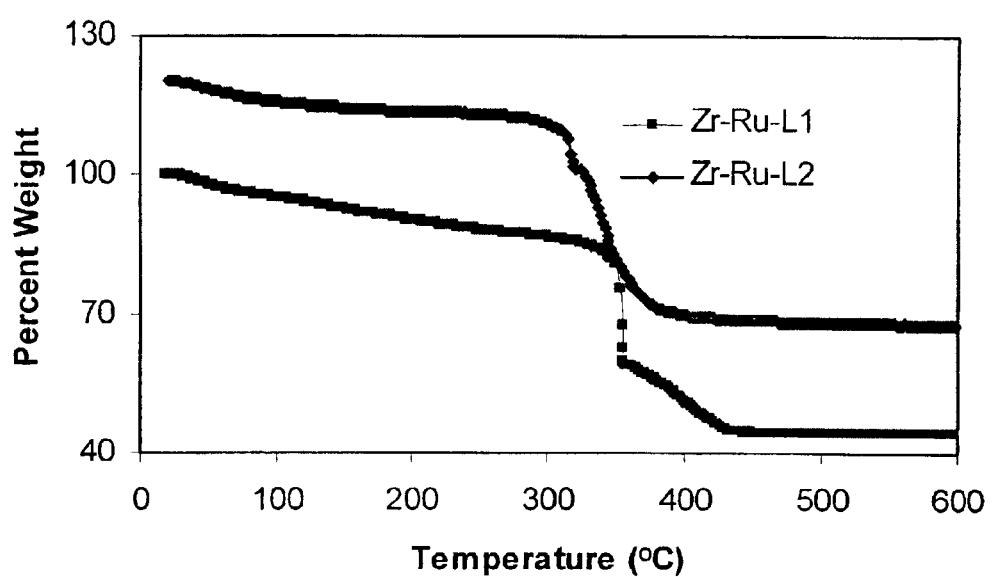
FIG. 2 is a graph illustrating the TGA curves of Zr—Ru—$L_1$ and Zr—Ru—$L_2$ as obtained by the experimental procedures described in Example 1.
Figure 3:
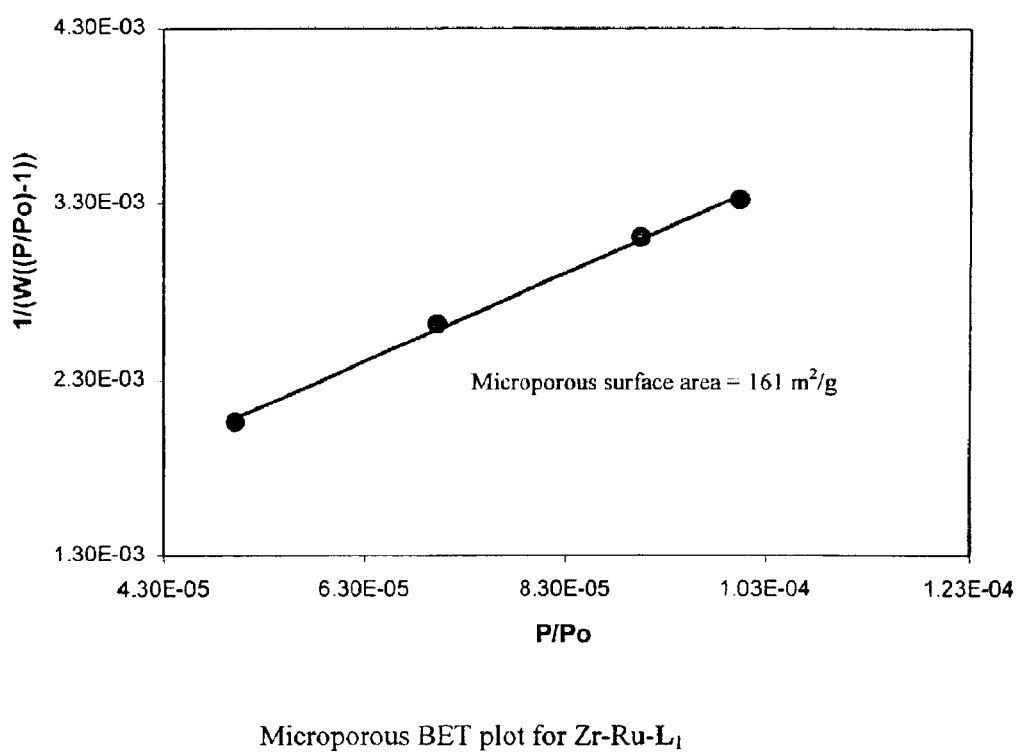
FIG. 3 is a microporous BET plot for Zr—Ru—$L_1$ as obtained by the experimental procedures described in Example 1.
Figure 4:
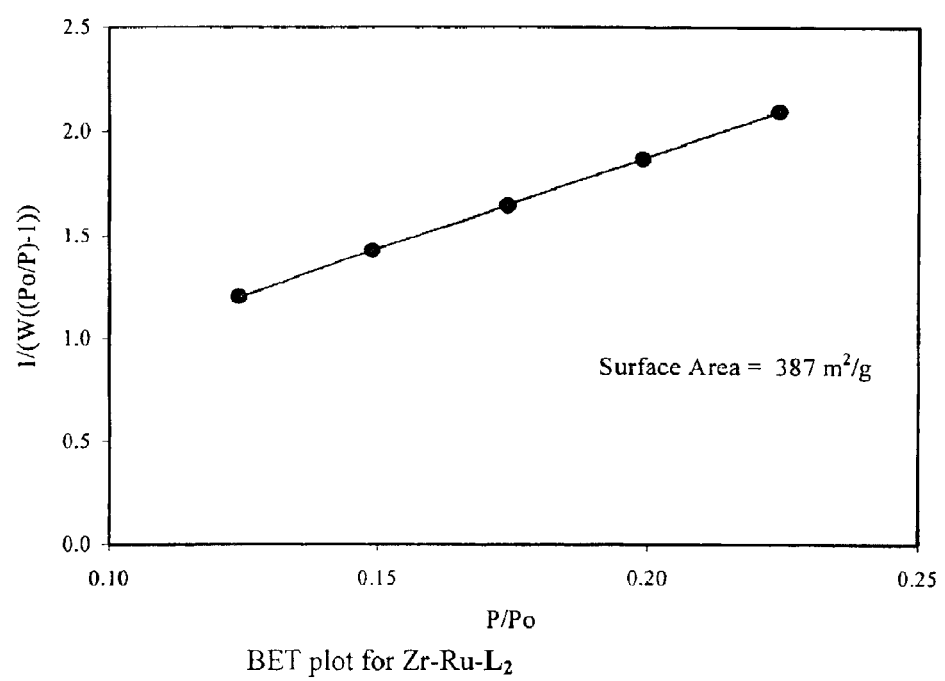
FIG. 4 is a BET plot for Zr—Ru—$L_2$ as obtained by the experimental procedures described in Example 1.
Figure 5:
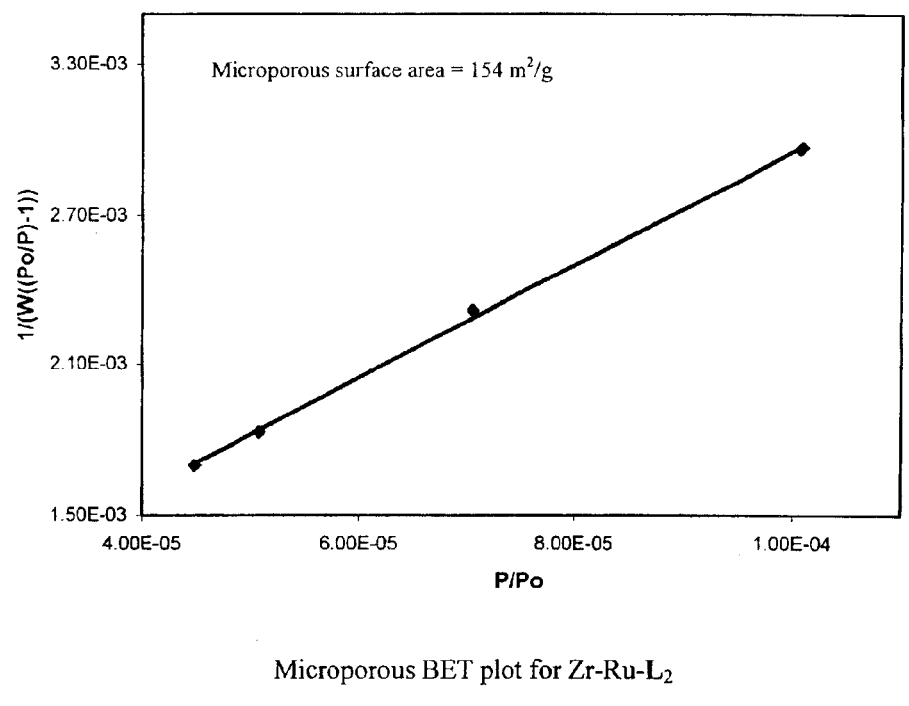
FIG. 5 is a microporous BET plot for Zr—Ru—$L_2$ as obtained by the experimental procedures described in Example 1.
Figure 6:
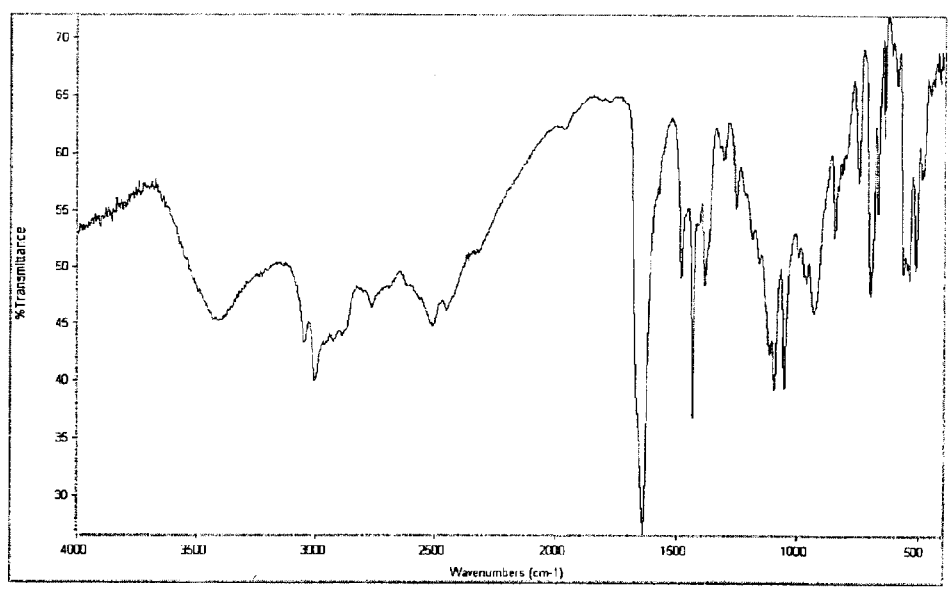
FIG. 6 is a graphical representation of an FT-IR spectrum of Ru($L_1$—$H_4$)(DMF)$_2$Cl$_2$ as obtained by the experimental procedures described in Example 1.
Figure 7:
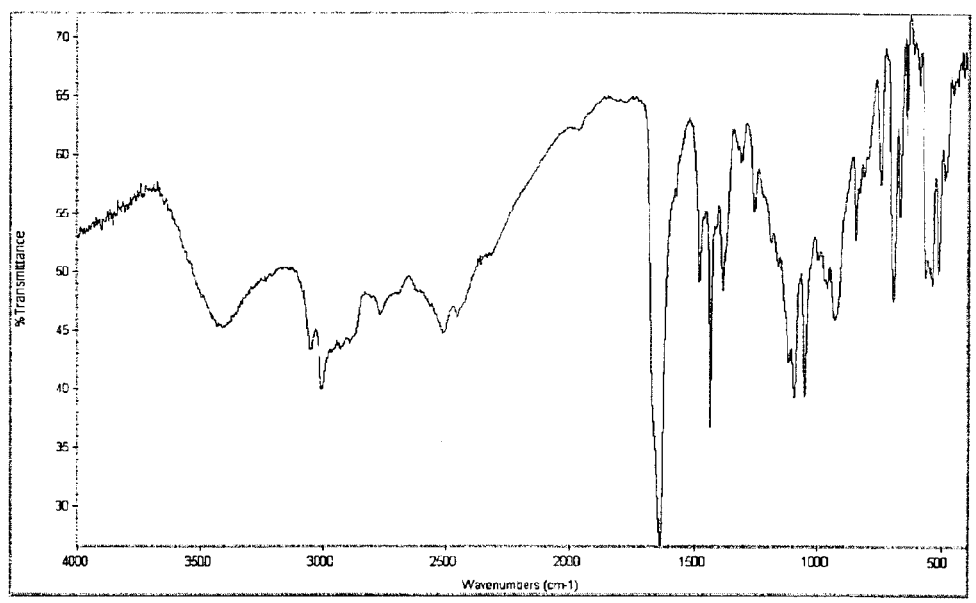
FIG. 7 is a graphical representation of an FT-IR spectrum of Zr—Ru—$L_1$ as obtained by the experimental procedures described in Example 1.
Figure 8:
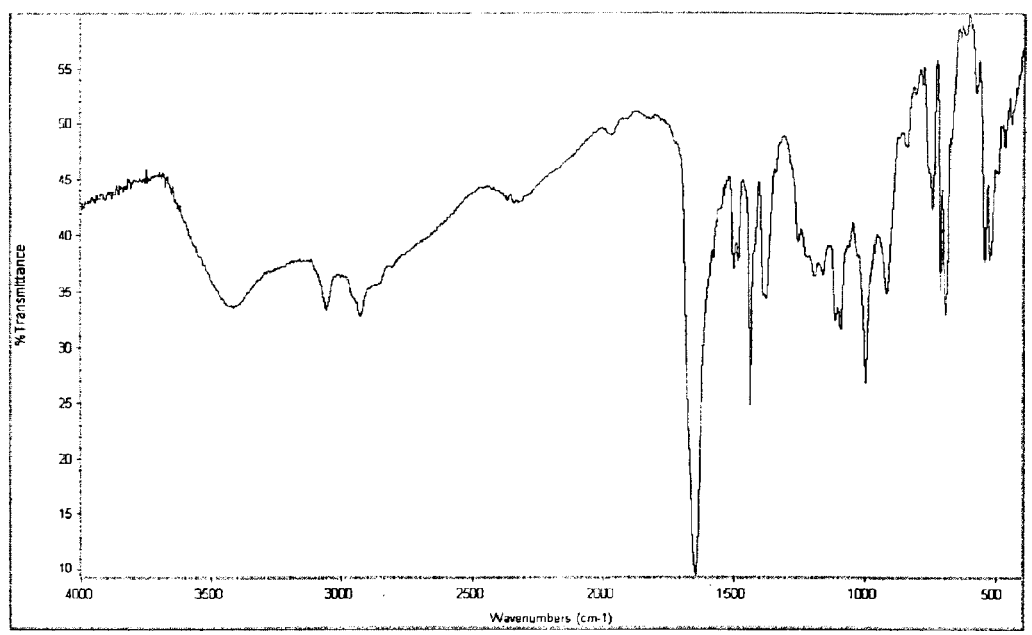
FIG. 8 is a graphical representation of an FT-IR spectrum of Ru($L_2$—$H_4$)(DMF)$_2$Cl$_2$ as obtained by the experimental procedures described in Example 1.
Figure 9:
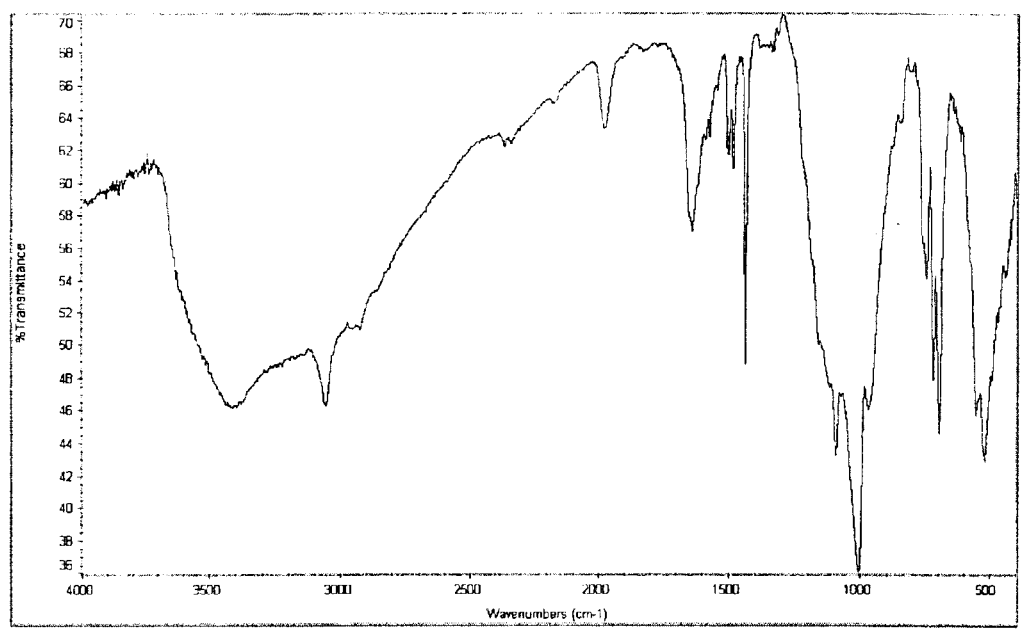
FIG. 9 is a graphical representation of an FT-IR spectrum of Zr—Ru—$L_2$ as obtained by the experimental procedures described in Example 1.

Chiral porous metal phosphonates, methods for producing chiral porous metal phosphonates and methods for using chiral porous metal phosphonates as heterogeneous asymmetric catalysts are provided. The term catalyst as used throughout includes a precatalyst.

It has now been discovered that the chiral porous metal phosphonates according to the present invention may provide excellent enantioselectivity in asymmetric reactions. Previous attempts to immobilize and/or heterogenize a homogeneous catalyst have typically resulted in a drop in enantiomeric excess (e.e.). It has now been found that an asymmetric homogeneous catalyst may be heterogenized and immobilized by reacting a phosphonic acid derivative of the homogeneous catalyst with a metal source. The metal source may include those metal compounds wherein the metal can participate in the formation of a metal phosphonate solid, such as metal alkoxides, metal halides and the like. The resulting porous hybrid solid metal phosphonate functions well as a heterogeneous asymmetric catalyst in asymmetric reactions such as asymmetric hydrogenation without a drop in e.e. or with an improvement over the results obtained with a parent homogeneous catalyst. The chiral porous metal phosphonate may be produced, for example, using a molecular building block approach by combining homogeneous catalysts modified with phosphonic acids or other groups with a metal source such as metal alkoxides or metal halides to provide a heterogeneous asymmetric catalyst. This general method will allow the incorporation of various metal-organic framework structures as well as a variety of platinum group metals and their complexes which are active as homogeneous asymmetric catalysts.

Homogeneous catalysts are known in the art. Examples of homogeneous catalysts include transition metal complexes such as platinum group metal complexes and the like. Preferably, the homogeneous catalysts are metal complexes of platinum group metals, by way of example, ruthenium-, rhodium-, iridium-, or palladium-based asymmetric complex catalysts. Other examples include ruthenium-, rhodium- or iridium-phosphine complexes, particularly those metal complexes with chiral bisphosphine moieties. Preferably, the homogeneous catalysts are ruthenium complexes which include a biaryl bisphosphine moiety, such as a Ru-BINAP complex, a Rh-BINAP complex, or a palladium-MOP complex (where MOP is 2-methoxy-2'-diphenylphosphino-1,1'-binaphthalene).

In a preferred aspect of the invention, the homogeneous catalysts contain a chiral bisphosphine moiety. In one aspect, metal phosphonates containing a pendant chiral chelating bisphosphine can be prepared. By way of example, rigid bisphosphonic acid ligands containing bisphosphine moieties, 2,2'-bis(diphenylphosphino)-1,1'-binaphthyl-6,6'-bis(phosphonic acid), $L_1$—$H_4$, and 2,2'-bis(diphenylphosphino)-1,1'-binaphthyl-4,4'-bis(phosphonic acid), $L_2$—$H_4$, may be used.

These rigid bisphosphonic acid ligands may be reacted first with an appropriate metal complex such as a platinum group metal complex wherein the metal is ruthenium, rhodium, iridium, osmium, palladium or platinum, and then with a metal alkoxide or other metal source to form a chiral porous metal phosphonate useful as a heterogeneous asymmetric catalyst. Such hybrid materials combine the thermally and oxidatively stable framework structure of metal phosphonates and enantioselectivity of metal complexes containing pendant chiral bisphosphines, and are useful in heterogeneous asymmetric catalysis.

Bisphosphonic acid ligands may be prepared from any number of biaryl bisphosphines and bipyridyl bisphosphines known in the art. Preferably, the bisphosphonic acid ligands are prepared from chiral or optically active phosphine moieties. Such phosphine moieties may include, for example, 2,2'-bis-(diphenylphosphino)-1,1'-binaphthyl (BINAP), or other BINAP derivatives, such as derivatives in which the naphthalene ring of BINAP is partially reduced, such as each optical isomer of 2,2'-bis(diphenylphosphino)-5,5',6,6',7,7',8,8'-octahydro-1,1'-binaphthyl (abbreviated name: $H_8$BINAP); or BINAP derivatives in which the naphthalene ring of BINAP carries substituent(s), such as each optical isomer of 2,2'-bis-(diphenylphosphino)-6,6'-dimethyl-1,1'-binaphthyl (abbreviated name: 6MeBINAP), or 2,2'-Dimethyl-6,6'-bis(diphenylphosphino)biphenyl (BIHEMP) or (6,6'-dimethoxybiphenyl-2,2'-diyl)bis(diphenylphosphine) (MeO-BIPHEP), 2,2',6,6'-tetramethoxy-4,4'-bis(diphenylphosphino)-3,3'-bipyridine (Py-Phos), or the like. Preferably, the bisphosphine moiety will be BINAP.

The platinum group metal complex may include any appropriate platinum group metal, preferably ruthenium, rhodium, iridium, osmium, platinum or palladium, more preferably, ruthenium, rhodium, iridium or palladium. The metal complex may be any known to those of skill in the art of homogeneous catalysts such as metal complex compounds coordinated with aromatic compounds. Specific examples include ruthenium complex compounds coordinated with aromatic compounds such as [ruthenium(benzene)dichloride]dimer, [ruthenium(p-cymene)dichloride]dimer, [ruthenium(trimethylbenzene)dichloride] dimer, and [ruthenium(hexamethylbenzene)dichloride] dimer, $PtCl_2$, $H_2PtCl_4$; $Pd_2(DBA)_3$; $Pd(OAc)_2$; $PdCl_2(RCN)_2$; $(Pd(allyl)Cl_2)$; $Pd(PR_3)_4$; $(Rh(NBD)_2)X$; (Rh(NBD)Cl)$_2$; $(Rh(COD)Cl)_2$; $(Rh(COD)_2)X$; $Rh(acac)(CO)_2$; $Ph(ethylene)_2(acac)$; $(Rh(ethylene)_2Cl)_2$; $RhCl(PPh_3)_3$; $Rh(CO)_2Cl_2$; $RuHX(L)_2$(diphosphine); $RUX_2(L)_2$(diphosphine); $Ru(Arene)X_2$(diphosphine), $Ru(RCOO)_2$(diphosphine); $Ru(methallyl)_2$(diphosphine); Ru(aryl group)$X_2(PPh_3)_3$; $Ru(COD)(COT)$, $Ru(COD)(COT)X$; Ru(aryl group)$X_2$(diphosphine), $RuCl_2(COD)_2$, $RUX_2$(diphosphine), $RuCl_2(=CHR)(PR_3)_2$; $Ru(ArH)Cl_2$; $Ru(COD)(methallyl)_2$; $(Ir(NBD)_2Cl)_2$; $(Ir(NBD)_2)X$; (Ir(COD)$_2$Cl)2; $(Ir(COD)_2)X$; wherein each R is independently selected from the group consisting of: alkyl or aryl; Ar is an aryl group and X is a counteranion such as halides, pseudo-halides, $BF_4^-$, $PF_6^-$, $AsF_6^-$ and the like, and L is a coordination solvent or other ligands such as DMF, acetonitrile, THF, ether, methanol, or acetone.

In one aspect, the metal phosphonates will further contain a diamine moiety. In one aspect, the homogeneous asymmetric catalyst contains a diamine moiety. In another aspect of the invention, the bisphosphonic ligand is reacted with the metal complex and a diamine ligand. The diamine ligand can be any such ligand known in the art. Examples include methylenediamine, ethylenediamine, 1,2-diaminopropane, 1,3-diaminopropane, 1,4-diaminobutane, 2,3-diaminobutane, 1,2-cyclopentanediamine, 1,2-cyclohexanediamine, 1,1-diphenylethylenediamine, 1,1-di(p-methoxyphenyl)ethylenediamine, 1,1-di(3,5-dimethoxyphenyl)ethylenediamine, and 1,1-dinaphthylethylenediamine. Optically active diamine compounds may be also used. Examples thereof include, for example, optically active 1,2-diphenylethylenediamine (abbreviated name: DPEN), 1,2-di(p-methoxyphenyl)ethylenediamine, 1,2-cyclohexanediamine, 1,2-cycloheptanediamine, 2,3-dimethylbutanediamine, 1-methyl-2,2-diphenylethylenediamine, 1-isobutyl-2,2-diphenylethylenediamine, 1-isopropyl-2,2-diphenylethylenediamine, 1-benzyl-2,2-diphenylethylenediamine, 1-methyl-2,2-di(p-methoxyphenyl)ethylenediamine (abbreviated name: DAMEN), 1-isobutyl-2,2-di(p-methoxyphenyl)- ethylenediamine (abbreviated name: DAIBEN), 1-isopropyl-2,2-di(p-methoxyphenyl)ethylenediamine (abbreviated name: DAIPEN), 1-benzyl-2,2-di(p-methoxyphenyl)ethylenediamine, 1-methyl-2,2-di(3,5-dimethoxyphenyl)ethylenediamine, 1-isopropyl-2,2-di(3,5-dimethoxyphenyl)ethylenediamine, 1-isobutyl-2,2-di(3,5-dimethoxyphenyl)ethylenediamine, 1-benzyl-2,2-di(3,5-dimethoxyphenyl)ethylenediamine, 1-methyl-2,2-dinaphthylethylenediamine, 1-isobutyl-2,2-dinaphthylethylene-diamine, 1-isopropyl-2,2-dinaphthylethylenediamine, and 1-benzyl-2,2-dinaphthylethylenediamine. Preferred diamine ligands include DPEN, DAIBEN and DAIPEN.

Typically, in the methods described, the homogeneous catalysts are derivatized with phosphonic acid prior to being reacted with a metal source such as a metal alkoxide or metal halide. This step may involve reacting a compound containing a phosphonic acid group such as the rigid bisphosphonic acid ligands, 2,2'-bis(diphenylphosphino)-1,1'-binaphthyl-6,6'-bis(phosphonic acid), $L_1$—$H_4$, and 2,2'-bis(diphenylphosphino)-1,1'-binaphthyl-4,4'-bis(phosphonic acid), $L_2$—$H_4$, with a metal compound or complex to form the derivatized homogeneous catalyst. Such processes are known in the art or can be developed based on known concepts.

The metal source used for reaction with the derivatized homogeneous asymmetric catalyst may be any metal source which will result in a solid metal phosphonate upon reaction. Such metal sources include metal alkoxides, metal halides and the like. In a preferred aspect of the invention, a metal alkoxide is used, the metal is Zr, Ti or Hf, and the alkoxide has between 1–10 carbon atoms. In a most preferred aspect of the invention, the metal is zirconium and the alkoxide has between one and five carbon atoms. In a particularly preferred aspect, the metal alkoxide is zirconium tetra(tert-butoxide), $Zr(O^tBu)_4$, or zirconium tetra(n-butoxide), $Zr(OBu)_4$.

The reaction conditions for reacting the metal alkoxide with a derivatized homogeneous asymmetric catalyst to obtain a chiral porous metal phosphonate will depend upon the metal alkoxide and the homogeneous asymmetric catalyst being reacted. Typically, the reaction conditions will require refluxing in a solvent under inert atmosphere.

In one aspect of the invention, chiral porous metal phosphonates which may be used as heterogeneous asymmetric catalysts are provided according to Formula I:

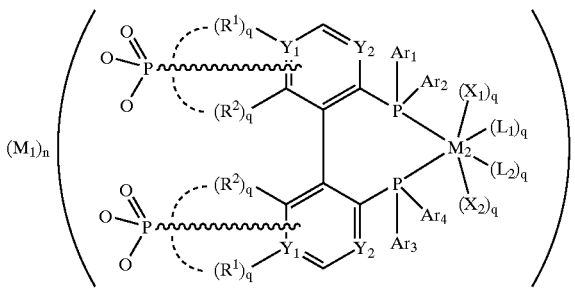

Formula I wherein $M_1$ is a group IV metal, a lanthanide metal, or any other first-row transition metal atom, n=1–2 and is a quantity such that Formula I retains charge neutrality regardless of the $M_1$ atom used;

$M_2$ is Ru, Rh, Ir, Os, Pt or Pd;

$X_1$ and $X_2$ may be covalently or ionically bonded to the $M_2$ center, and may each independently represent an anionic radical, preferably hydrogen, halogen, an alkoxy group, or a carboxyl group, or may be another anionic radical such as $BF_4^-$, $PF_6^-$, $AsF_6^-$ and the like;

$Ar_1$, $Ar_2$, $Ar_3$ and $Ar_4$ independently represent a phenyl group substituted with from zero to five substituents selected from straight-chain or branched-chain lower alkyl group, halogen, or lower alkoxy group;

$L_1$ and $L_2$ independently represent a coordinated solvent molecule, such as DMF, or $L_1$ and $L_2$ represent donor atoms comprising half of a diamine moiety such that $L_1$ and $L_2$ are joined to give a chelating diamine, or $L_1$ and $L_2$ represent a weakly coordinating ligand, such as an olefin, by way of example, $L_1$ and $L_2$ together may represent cyclooctadiene or norbornene;

$Y_1$ and $Y_2$ represent a carbon or nitrogen atom;

$R^1$ and $R^2$ independently represent hydrogen, a lower alkyl group, or a lower alkoxy group, or each pair of $R^1$ and $R^2$ can be the same or different and are bonded such that each $R^1$ and $R^2$ together with the attached ring form a ring selected from a substituted or unsubstituted tetrahydronaphthalene ring, a substituted or unsubstituted naphthalene ring, or a substituted or unsubstituted 1,3-benzodioxole ring, provided, however, that when $Y_1$ is N, $R^1$ is nothing;

P$\sim\!\sim\!\sim$ represents a bond independently linking the phosphonate groups to the benzene, pyridine or pyrimidine ring or a ring formed by each of $R^1$ and $R^2$ as defined above, in any of the reasonable positions either directly or through one of the following linkages:

an alkene group, an alkyl group, an aryl group or a styryl group; and each q is independently selected from 0 or 1.

As one of skill in the art will understand, the presence or absence of various substituents will be determined in some aspects by the metals selected. As used herein, alkyl or alkoxy includes a branched or straight chain group having from about 1 to 10 carbon atoms; lower alkyl or lower alkoxy includes a branched or straight chain group having from about 1 to 5 carbon atoms; and aryl means a substituted or unsubstituted phenyl group. Substituents for substituted elements may include straight-chain or branched-chain lower alkyl groups, halogen or lower alkoxy groups, among others.

In one aspect, $Ar_1=Ar_3$ and $Ar_2=Ar_4$. In one preferred aspect, $Ar_1=Ar_2=Ar_3=Ar_4$ and Ar is an unsubstituted phenyl group.

In another preferred aspect, $Y_1$ and $Y_2$ are C and each of $R^1$ and $R^2$ are bonded together with the attached benzene ring to form a naphthalene ring.

In a still further aspect, $M_1$ is Ti, Zr or Hf.

In a further aspect, $M_2$ is Rh, $L_1$ and $L_2$ represent coordinating solvent molecules or weakly coordinating ligands such as olefins (by way of example, $L_1$ and $L_2$ together represent a COD or NBE molecule) and either $X_1$ or $X_2$ represents an anionic radical (q is 0 for the other X component).

In another preferred aspect, the chiral porous metal phosphonates are selected from one of the following formulas A–D:

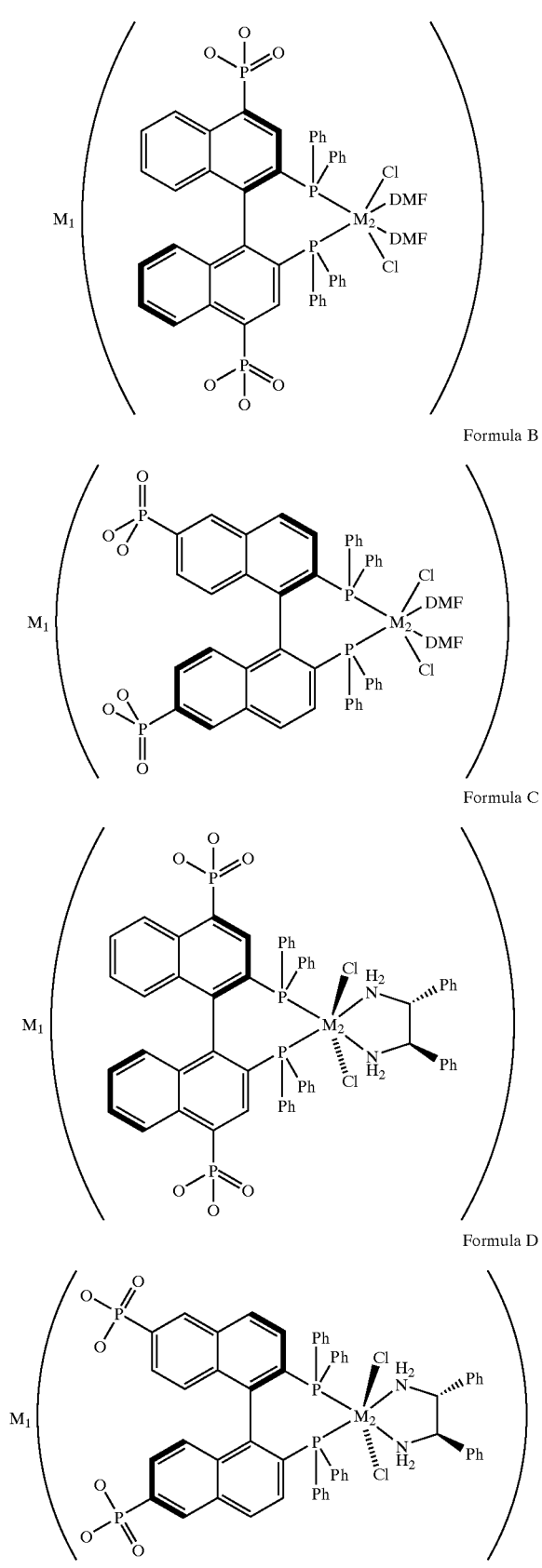

Formula A

Formula B

Formula C

Formula D wherein $M_1$ is Zr, Ti or Hf and $M_2$ is Ru or Os. The opposite enantiomers of the bisphosphines are also utilized to produce chiral products with opposite handedness.

In a more preferred aspect of the invention, $M_2$ is Ru. In a most preferred aspect of the invention, $M_1$ is Zr and $M_2$ is Ru.

The chiral porous metal phosphonates of the invention may be produced according to the methods described above, and typically possess very high surface areas (~500 m²/g) and can be either polycrystalline or amorphous as judged by powder X-ray diffraction studies. These chiral porous solids are typically featureless in scanning electron micrographs and are typically built from submicron particulates.

The chiral porous metal phosphonates of the invention are particularly useful as heterogeneous catalysts in asymmetric reactions. The metal phosphonates may be employed in a variety of asymmetric reactions such as asymmetric hydrogenation, hydride transfer reaction, hydrosilylation, hydroboration, hydrovinylation, hydrocarboxylation, isomerization, allylic alkylation, cyclopropanation, Diels-Alder reaction, Alder-ene reaction, Aldol reaction, Heck reaction or Michael addition, and the like.

Some of these reactions may be represented as follows:

Asymmetric hydrogenation:

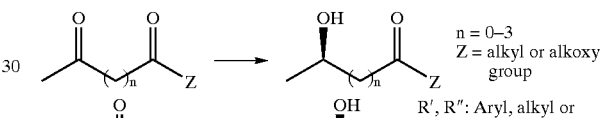

n = 0–3
Z = alkyl or alkoxy group

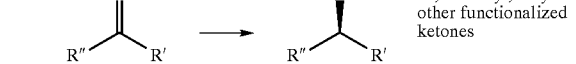

R', R": Aryl, alkyl or other functionalized ketones

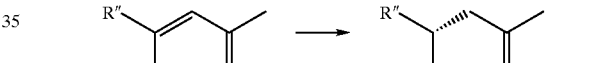

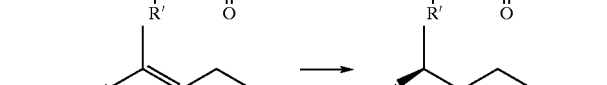

Z = Ar, H₂COOR
R' = H, alkyl etc.

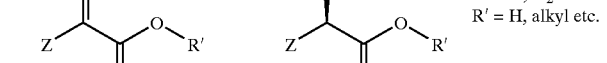

Olefin isomerization

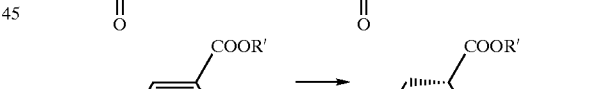

Diels-Alder reaction

Aldol addition

Heck reaction

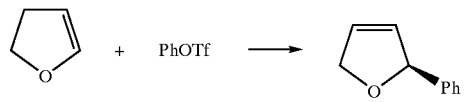

Alder-ene reaction

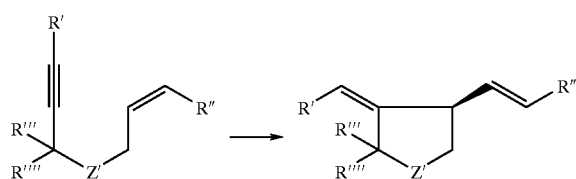

The invention provides, in one aspect, a method for preparing an asymmetric compound comprising contacting a substrate capable of forming an asymmetric product by an asymmetric reaction with a chiral porous metal phosphonate comprising the reaction product of a metal source and a phosphonic acid derivative of a homogeneous asymmetric catalyst. Preferably, the metal source is a metal alkoxide or a metal halide. More preferably, the metal source is a metal alkoxide which comprises a metal selected from Ti, Zr or Hf and an alkoxide with 1–10 carbon atoms. In a most preferred aspect, the metal alkoxide is a zirconium alkoxide with one to five carbon atoms. The homogeneous asymmetric catalyst is preferably a ruthenium complex containing a chiral bisphosphine moiety. Substrates possessing functionality such that the substrate is capable of forming an asymmetric product by an asymmetric reaction include unsaturated compounds, β-keto esters, β-diketones, aromatic ketones, imines, oximes and the like.

In one aspect, a method for preparing an asymmetric compound comprises contacting a substrate capable of forming an asymmetric product by an asymmetric reaction with a chiral porous metal phosphonate according to Formula I. In a preferred aspect of the invention, a method for preparing an asymmetric compound comprises contacting a substrate capable of forming an asymmetric product by an asymmetric reaction with a chiral porous metal phosphonate according to Formula A, B, C or D. Reaction conditions for carrying out such asymmetric reactions are known to those of skill in the art.

In another aspect of the invention, a method is provided for the stereoselective hydrogenation of a substrate capable of forming an asymmetric product by hydrogenation comprising contacting the substrate with a chiral porous metal phosphonate comprising the reaction product of a metal source and a homogeneous asymmetric catalyst. Preferably, the metal source is a metal alkoxide or a metal halide. More preferably, the metal source is a metal alkoxide which comprises a metal selected from Ti, Zr or Hf and an alkoxide with 1–10 carbon atoms. In a most preferred aspect, the metal alkoxide is a zirconium alkoxide with one to five carbon atoms. The homogeneous asymmetric catalyst is preferably a ruthenium complex containing a chiral bisphosphine moiety.

In another aspect of the invention, a method is provided for the stereoselective hydrogenation of a substrate capable of forming an asymmetric product by hydrogenation comprising contacting the substrate with a chiral porous metal phosphonate according to Formula I. In a preferred aspect of the invention, a method is provided for the stereoselective hydrogenation of a substrate capable of forming an asymmetric product by hydrogenation comprising contacting the substrate with a chiral porous metal phosphonate according to Formula A, B, C or D. Reaction conditions for carrying out such hydrogenation reactions are known to those of skill in the art.

The methods and metal phosphonates of the invention provide heterogeneous catalysts for a variety of asymmetric reactions. Without being bound by any theory, the metal phosphonates are believed to provide a highly porous catalyst surface which enables the transport of the asymmetric substrate reactant and produces an asymmetric product without a substantial reduction of e.e. over known methods using homogeneous catalysts. Ready tunability of the molecular building block approach of the invention allows the optimization of the catalytic performance of these hybrid materials and provides practically useful heterogeneous asymmetric catalysts. Additionally, the metal phosphonates may be reused and recycled without substantial loss of activity.

The invention will now be more fully explained by the following examples. However, the scope of the invention is not intended to be limited to these examples.

EXAMPLES

Example 1

Scheme 1 illustrates a process for obtaining a chiral porous metal phosphonate according to the present invention.

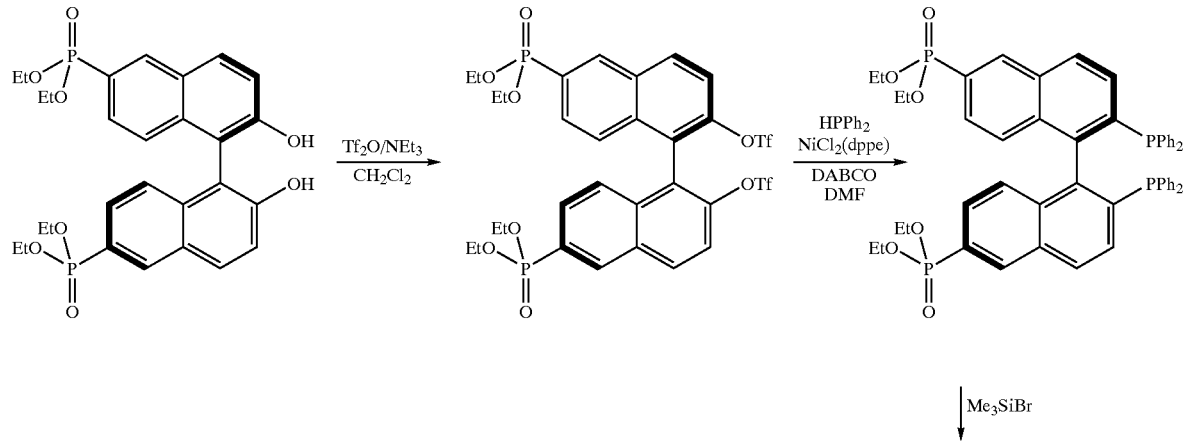

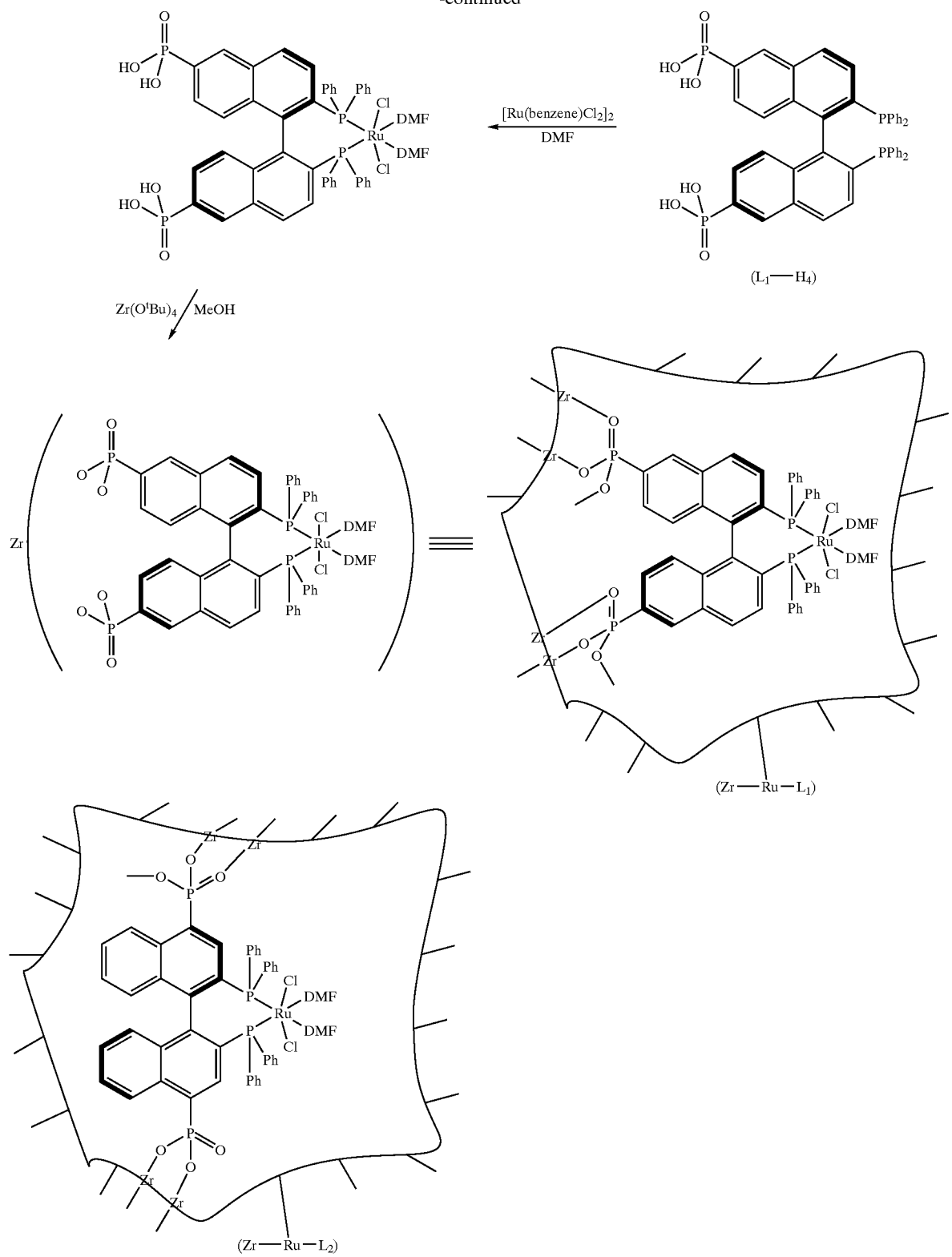

Enantiopure $L_1$—$H_4$ was synthesized in 3 steps starting from 2,2'-dihydroxy-1,1'-binaphthyl-6,6'-bis(diethylphosphonate) ) in 44% overall yield (Scheme 1). Phosphiation of 2,2'-bis(triflato)-1,1'-binaphthyl-bis(diethylphosphonate) was Ni-catalyzed. All the intermediates and $L_1$—$H_4$ were characterized by $^1H$, $^{13}C\{^1H\}$, and $^{31}P\{^1H\}$ NMR spectroscopies and mass spectrometry. $L_2$—$H_4$ was synthesized according to a literature procedure. (M. Kant et al., *Eur. J. Org.* 477 (2001)).

Ru(L$_1$—H$_4$)(DMF)$_2$Cl$_2$ and Ru(L$_2$—H$_4$)(DMF)$_2$Cl$_2$ intermediates were synthesized by treating L$_1$—H$_4$ and L$_2$—H$_4$ with 0.46 equiv of [Ru(benzene)Cl$_2$]$_2$ in DMF at 100° C., respectively. Chiral porous zirconium phosphonates with approximate formulae Zr[Ru(L$_1$)-DMF)$_2$Cl$_2$].2MeOH (Zr—Ru—L$_1$) and Zr[Ru(L$_2$)DMF)$_2$Cl$_2$].2MeOH (Zr—Ru—L$_2$) were synthesized by refluxing Zr(O$^t$Bu)$_4$ and 1 equiv of Ru(L$_1$—H$_4$)(DMF)$_2$Cl$_2$ and Ru(L$_2$—H$_4$)(DMF)$_2$Cl$_2$ in methanol, respectively. These chiral porous zirconium phosphonates have been characterized with a variety of techniques including TGA, nitrogen adsorption isotherms, XRD, SEM, IR, and microanalysis. (FIGS. 1–11).

Figure 10:
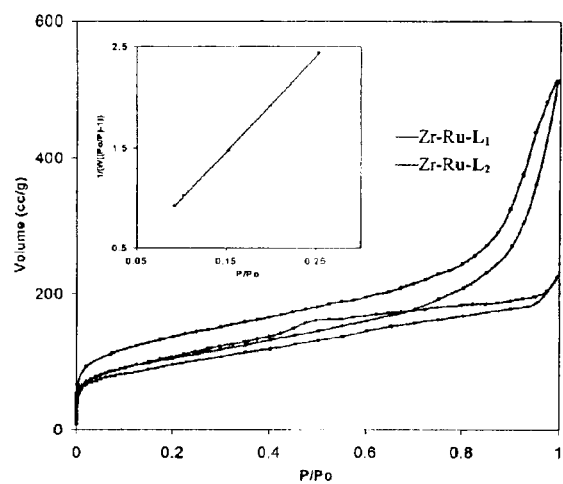
FIG. 10 is a graphical representation of $N_2$ adsorption isotherms for Zr—Ru—$L_1$ and Zr—Ru—$L_2$ at 77K. The inset shows a BET plot for Zr—Ru—$L_1$ in the mesoporous region. The experimental procedures are described in Example 1.
Figure 11:
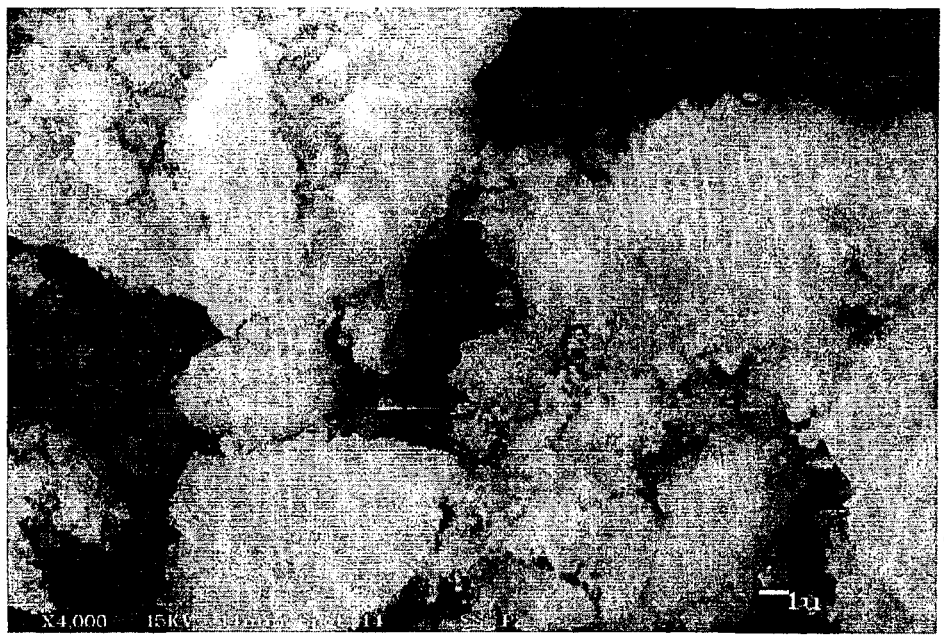
FIG. 11 is a scanning electron micrograph (SEM) of Zr—Ru—$L_1$ as obtained by the experimental procedures described in Example 1.

While the compositions of Zr—Ru—L$_1$ and Zr—Ru—L$_2$ were established by TGA (FIG. 2) and microanalysis results, the IR spectra (FIGS. 6–9) supported the formation of zirconium phosphonate bonds as the P—O stretches at 950–1150 cm$^{-1}$ have shifted to lower wave numbers compared to those of Ru(L$_1$—H$_4$)(DMF)$_2$Cl$_2$ and Ru(L$_2$—H$_4$)(DMF)$_2$Cl$_2$. The IR spectra also exhibit intense and broad O—H stretching vibrations at ~3400 cm$^{-1}$, consistent with the presence of MeOH solvates. Nitrogen adsorption measurements indicate that both Zr—Ru—L$_1$ and Zr—Ru—L$_2$ are highly porous with rather wide pore size distributions (FIG. 10). Zr—Ru—L$_1$ exhibits a total BET surface area of 475 m$^2$/g with a microporous surface area of 161 m$^2$/g (FIG. 3) and a pore volume of 1.02 cm$^3$/g (by BJH method). Zr—Ru—L$_2$ exhibits a total BET surface area of 387 m$^2$/g (FIG. 4) with a microporous surface area of 154 m$^2$/g (FIG. 5) and a pore volume of 0.53 cm$^3$/g (by BJH method). SEM images show that both solids are composed of submicrometer particles (FIGS. 1 and 11), while powder x-ray diffraction (PXRD) indicate that both solids are amorphous.

Although the amorphous nature of the present chiral porous zirconium phosphonates prevents elucidating their exact structures, the BINAP-Ru moieties on the surfaces have been successfully utilized for heterogeneous asymmetric catalysis. As Table 1 shows, both Zr—Ru—L$_1$ and Zr—Ru—L$_2$ are highly active catalysts for asymmetric hydrogenation of β-keto esters. Zr—Ru—L$_1$ catalyzes the hydrogenation of a wide range of β-alkyl-substituted β-keto esters with complete conversions and e.e.'s ranging from 91.7 to 95.0% with the same handedness of enantio-enrichment as the parent homogeneous BINAP-Ru catalyst. This level of enantioselectivity is only slightly lower than that of their best homogeneous counterparts. Similar to the BINAP-Ru catalyst, Zr—Ru—L$_1$ catalyzes the hydrogenation of β-aryl-substituted β keto esters with modest e.e. In contrast, Zr—Ru—L$_2$ catalyzes the hydrogenation of β keto esters with only modest e.e. values. This observation shows that the nature of derivation of the homogeneous catalytic systems can profoundly influence the performance of their heterogenized counterparts. Supernatants of Zr—Ru—L$_1$ and Zr—Ru—L$_2$ in MeOH did not catalyze the hydrogenation of β-keto esters, which unambiguously demonstrates heterogeneous nature of the present asymmetric catalytic systems.

TABLE 1

Heterogeneous Asymmetric Hydrogenation of β-Keto Esters[a]

| Substrate | Catalyst Loading | Temp | H$_2$ Pressure | Zr—Ru—L$_1$ e.e. (yield) | Zr—Ru—L$_2$ e.e. (yield) |
|---|---|---|---|---|---|
| (methyl acetoacetate) | 1% 1% | 60° C. rt | 700 (psi) 1400 | 94.0 (100) 95.0 (100) | 73.1 (90) |
| (ethyl 3-oxopentanoate) | 0.1% 1% | 60° C. rt | 700 1400 | 93.3 (100) 92.0 (100) | 65.0 (100) |
| (isopropyl acetoacetate) | 1% | rt | 1400 | 91.7 (100) | 68.1 (85) |
| (ethyl benzoylacetate) | 1% | rt | 1400 | 69.6 (100) | 15.7 (50) |
| (tert-butyl acetoacetate) | 1% | rt | 1400 | 93.1 (100) | 64.0 (100) |

TABLE 1-continued

Heterogeneous Asymmetric Hydrogenation of β-Keto Esters[a]

$$R_1 \underset{O}{\overset{O}{\bigcup}} \underset{O}{\overset{O}{\bigcup}} O^{R_2} + H_2 \xrightarrow[\text{CH}_3\text{OH}]{\text{Zr—Ru—(R)—L}_1 \text{ or Zr—Ru—(R)—L}_2} R_1 \underset{OH}{\overset{OH}{\bigcup}} \underset{O}{\overset{O}{\bigcup}} O^{R_2}$$

| Substrate | Catalyst Loading | Temp | H₂ Pressure | Zr—Ru—L₁ e.e. (yield) | Zr—Ru—L₂ e.e. (yield) |
|---|---|---|---|---|---|
| (methyl 2,2-dimethyl-3-oxobutanoate) | 1% | rt | 1400 | 93.3 (100) | 78.8 (70) |

[a]All the reactions were carried out in 20 h, and the e.e. values (%) were determined by GC on a Supelco γ - Dex 225 column. The absolute configurations of the products are identical to those obtained by the Ru—(R)-BINAP catalyst. The conversions were determined by the integrations of ¹H NMR spectra.

The Zr—Ru—L₁ system has been successfully reused for asymmetric hydrogenation of methyl acetoacetate without significant deterioration of enantioselectivity. The Zr—Ru—L₁ system was used for five cycles of hydrogenation with complete conversions and e.e. values of 93.5%, 94.2%, 94.0%, 92.4%, and 88.5%, respectively.

The Ru-containing chiral porous solids made were used for heterogeneous asymmetric hydrogenation of β-keto esters with up to 95% e.e. and can be readily recycled and reused.

Experimental Section.

Synthesis of Zr—Ru—L₁ solid precatalyst. L₁—H₄ was synthesized in three steps from 2,2'-dihydroxy-1,1'-binaphthyl-6,6'-bis(diethylphosphonate) and treated with 0.46 equiv. of [Ru(benzene)Cl₂]₂ in DMF at 100° C. under argon for 40 min and then cooled to 40° C. All the volatile components were removed under vacuum, and the dark-red solid was directly used for the synthesis of Zr—Ru—L₁ solid precatalyst. The above dark-red solid was first dissolved in anhydrous degassed methanol, and refluxed with 1 equiv. of Zr(O$^t$Bu)₄ overnight. After centrifugation and rinsing with anhydrous methanol for three times, the residue was dried under vacuum to gave a dark-brown solid in 96% yield. This dark-brown solid is not soluble in common organic solvents including methanol. Anal. calc. for $C_{52}H_{52}Cl_2N_2O_{10}P_4RuZr$, Zr[Ru(L₁)(DMF)₂Cl₂].2MeOH: C, 49.9; H, 4.19; N, 2.24; Cl, 5.66%. Found: C, 50.6; H, 3.87; N, 2.54; Cl, 4.98%.

General Procedure for Catalysis:

To solid precatalyst (6.0 mg, 5 μmole) in a test tube was added methyl acetoacetate (55 μL, 0.5 mmol) and anhydrous methanol (1 mL) under argon. The test tube was quickly transferred inside a stainless steel autoclave, and sealed. After purging with H₂ for 6 times, final H₂ pressure was adjusted to 1400 psi or 700 psi. H₂ pressure was released 20 hrs later, and methanol was removed in vacuo. The hydrogenated product was extracted with diethyl ether and passed through a mini silica-gel column. The conversions were assessed based on the integration of ¹H NMR peaks of the products and starting materials, while the e.e. values were determined using chiral GC.

Experimental Procedures.

1. Synthesis of 2,2'-bis(triflato)-1,1'-binaphthyl-6,6'-bis(diethylphosphonate)

To a 250 mL round bottom flask was added 2,2'-dihydroxy-1,1'-binaphthyl-6,6'-bis(diethylphosphonate) (7.00 g, 12.5 mmol), anhydrous dichloromethane (80 mL) and triethylamine (16.0 mL, 115 mmol) under Argon. This mixture was cooled down to −50° C. With vigorous stirring, trifluoromethanesulphonic anhydride (8.0 mL, 49 mmol) was added carefully (over a ~5 min period). The reaction mixture turned from pale yellow to dark red immediately, and the mixture was allowed to stir −50° C. for 1 hr and then warmed to room temperature and stirred overnight. TLC indicated complete conversion after 16 hrs. The reaction mixture was washed with water, saturated NaHCO₃, water and then dried with anhydrous MgSO₄. Silica-gel column chromatography with dichloromethane/acetone (5:1 v/v) gave 7.7 g (75%) of pure product as golden oil. ¹H{³¹P} NMR (CDCl₃): δ 8.59 (s, H₅), 8.27 (d, ³$J_{H-H}$=9.1 Hz, H₄), 7.71 (d, ³$J_{H-H}$=9.1 Hz, H₃), 7.69 (dd, ³$J_{H-H}$=8.8 Hz, ⁴$J_{H-H}$=1.4 Hz, H₇), 7.27 (d, ³$J_{H-H}$=8.8 Hz, H₈), 4.16 (m, —OCH₂CH₃), 1.33 (m, —OCH₂CH₃). ³¹P{¹H} NMR (CDCl₃): δ 17.6. ¹³C{¹H} NMR (CDCl₃): δ 146.8, 134.7, 134.2, 134.1, 133.3, 131.4, 131.2, 128.8, 128.7, 126.9, 126.8, 123.1, 120.4, 119.6, 62.6, 62.5, 16.3, 16.2. FAB MS: 823.0 (Calc. 822.6 for M⁺).

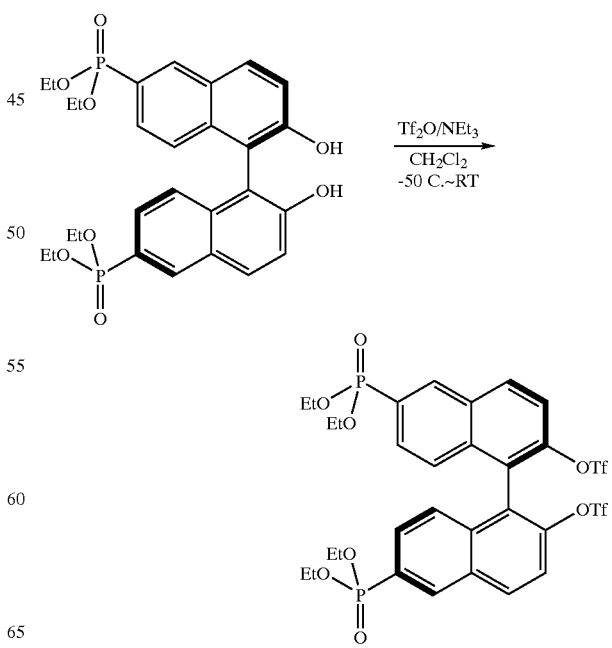

2. Synthesis of 2,2'-bis(diphenylphosphino)-1,1'-binaphthyl-6,6'-bis(phosphonic acid)

L$_1$—H$_4$. Under argon, HPPh$_2$ (0.5 mL, 3 mmol) was added to a DMF (20 mL) solution of Ni(dppe)Cl$_2$ (0.28 g, 0.51 mmol) in a 50 mL Schlenk flask. The resulting red suspension was heated at 100° C. for 0.5 hr, then followed by the addition of a DMF (15 mL) solution of 2,2'-bis(triflato)-1,1'-binaphthyl-6,6'-bis(diethylphosphonate) (4.1 g, 5.0 mmol) and DABCO (2.3 g, 20.5 mmol) via a cannula. The resulting greenish solution was kept at 100° C., and three additional portions of HPPh$_2$ (3×0.5 mL) were added by syringe 1 hr, 3 hr and 7 hr later. After 36 hrs, a large amount of solid has precipitated out. TLC indicated the disappearance of 2,2'-bis(triflato)-1,1'-binaphthyl-6,6'-bis(diethylphosphonate) after 48 hrs. The dark brown suspension was cooled to r.t., stirred for 1 h, and then the product was filtered under argon, washed with anhydrous DMF and acetone and dried in vacuo to give 2.6 g of partially deprotected 2,2'-bis(diphenylphosphino)-1,1'-binaphthyl-6,6'-bis(diethylphosphonate) as white powder. NMR spectra indicated that the ethoxy groups have been partially deprotected. $^1$H{$^{31}$P} NMR (d$_6$-DMSO): δ 8.33 (s, H$_5$), 7.99 (d, $^3J_{H\text{-}H}$=8.3 Hz, H$_4$), 7.43 (d, $^3J_{H\text{-}H}$=8.5 Hz, H$_7$), 7.21 (m, H$_3$ and Ph—H), 7.10 (m, Ph—H), 7.01 (m, Ph—H), 6.72 (d, $^3J_{H\text{-}H}$=8.5 Hz, H$_8$), 3.76 (m, —OCH$_2$CH$_3$), 1.18 (m, —OCH$_2$CH$_3$). $^{31}$P{$^1$H} NMR (d$_6$-DMSO): δ 13.6 and 19.4, −15.1 and −14.4.

Under argon, 2.6 g of partially deprotected 2,2'-bis(diphenylphosphino)-1,1'-binaphthyl-6,6'-bis(diethylphosphonate) was stirred with bromotrimethylsilane (10 mL) at r.t. overnight. Then the volatile was removed in vacuo and anhydrous methanol (20 mL) added, and the mixture was stirred for 10 min. All the volatiles were removed under vacuum to give pale yellow powder of L$_1$—H$_4$ (2.44 g, 62%). $^1$H{$^{31}$P} NMR (d6-DMSO): δ 8.29 (s, H$_5$), 8.16 (d, $^3J_{H\text{-}H}$=8.8 Hz, H$_4$), 7.36 (d, $^3J_{H\text{-}H}$=8.3 Hz, H$_7$), 7.23 (m, H$_3$ and Ph—H), 7.02 (m, Ph—H), 6.93 (m, Ph—H), 6.70 (d, $^3J_{H\text{-}H}$=8.3 Hz, H$_8$). $^{31}$P{$^1$H} NMR (d6-DMSO): δ 13.1, −15.3. $^{13}$C{$^1$H} NMR (CDCl$_3$): δ 144.0, 143.6, 136.7, 136.6, 136.5, 136.1, 136.0, 133.4, 133.3, 133.2, 133.1, 132.5, 132.4, 132.3, 132.0, 131.8, 131.4, 131.3, 131.2, 130.7, 129.1, 128.7, 128.4, 128.2, 126.9, 126.8, 126.2, 126.1, M.S.: 783.0 (Calc. M$^+$ 782.6), 822.9 (Calc. (M+K)$^+$ 821.7).

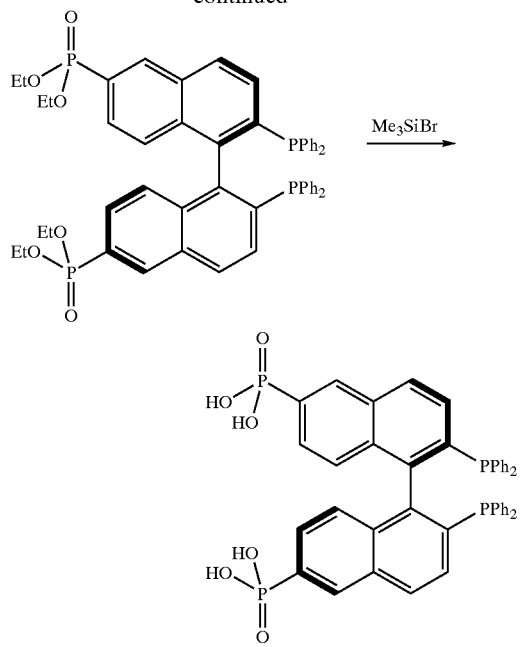

3. Synthesis of Zr[Ru(L$_1$)(DMF)$_2$Cl$_2$].2MeOH

A mixture of [Ru(benzene)Cl$_2$]$_2$ (Zelonka, R. A.; Baird. M. C. Can. J. Chem., 1972, 50, 3063) (46 mg, 0.092 mmole) and L$_1$—H$_4$ (156 mg, 0.2 mmol) in DMF (4 mL) was heated at 100° C. under argon for 40 min and then cooled to 40° C. All the volatile components were removed under vacuum and the dark-red solid was directly used for the formation of zirconium phosphonate.

To the dark red solid intermediate was added anhydrous degassed methanol (40 mL) and after 2 hrs of vigorous stirring, the solid slowly dissolved in methanol to give dark red solution. Zirconium tetra(tert-butoxide) (80 μL, 0.2 mmol) was then slowly added, and brown precipitate formed immediately. The resulting mixture was refluxed overnight. After centrifugation and rinsing with anhydrous methanol for three times, the residue was dried under vacuum to gave a dark-brown solid (240 mg, 96%). This dark-brown solid is not soluble in common organic solvents including methanol. Anal. calc. for C$_{52}$H$_{52}$Cl$_2$N$_2$O$_{10}$P$_4$RuZr, Zr[Ru(L$_1$)(DMF)$_2$Cl$_2$].2MeOH: C, 49.9; H, 4.19; N, 2.24; Cl, 5.66%. Found: C, 50.6; H, 3.87; N, 2.54; Cl, 4.98%.

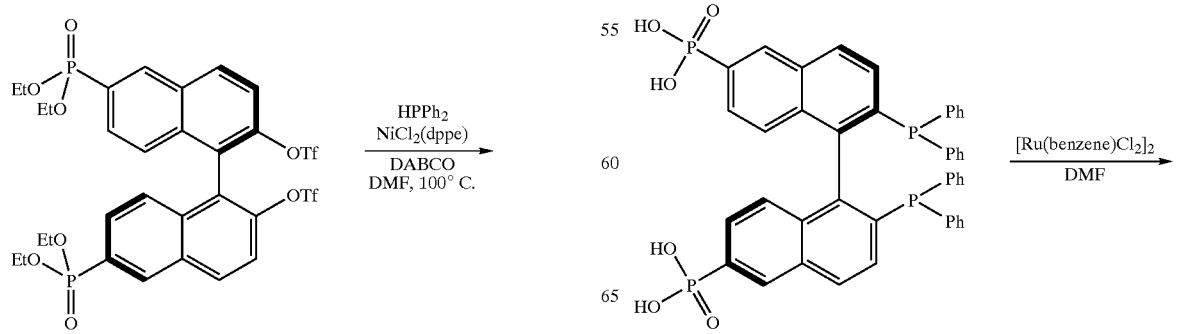

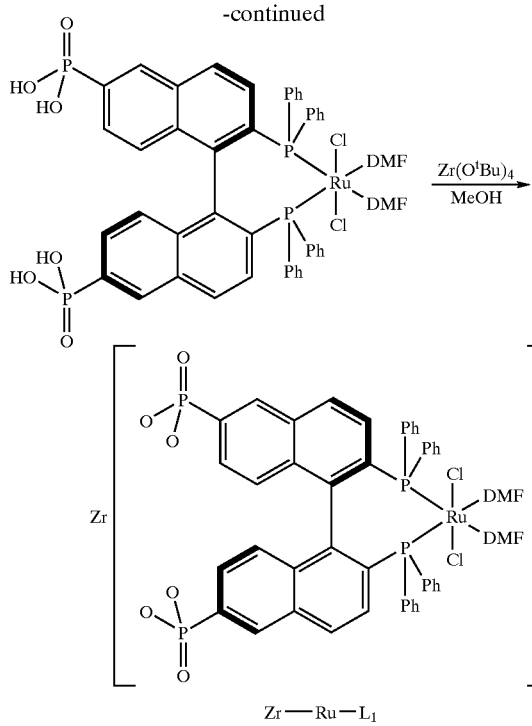

4. Synthesis of Zr[Ru(L$_2$)(DMF)$_2$Cl$_2$]·2MeOH

A mixture of [Ru(benzene)Cl$_2$]$_2$ (23 mg, 0.046 mmole) and L$_2$—H$_4$ (78 mg, 0.1 mmol) in DMF (2 mL) was heated at 100° C. under argon for 40 min and then cooled to 40° C. All the volatile components were removed under vacuum and the dark-red solid was directly used for the formation of zirconium phosphonate.

To the dark red solid intermediate was added anhydrous degassed methanol (20 mL) and after 2 hrs of vigorous stirring, the solid slowly dissolved in methanol to give dark red solution. Zirconium tetra(tert-butoxide) (40 μL, 0.1 mmol) was then slowly added, and brown precipitate formed immediately. The resulting mixture was refluxed overnight. After centrifugation and rinsing with anhydrous methanol for three times, the residue was dried under vacuum to gave a dark-brown solid (120 mg, 96%). This dark-brown solid is not soluble in common organic solvents including methanol. Anal. calc. for C$_{52}$H$_{52}$Cl$_2$N$_2$O$_{10}$P$_4$RuZr, Zr[Ru(L$_2$)(DMF)$_2$Cl$_2$]·2MeOH: C, 49.9; H, 4.19; N, 2.24; Cl, 5.66%. Found: C, 49.3; H, 3.89; N, 2.01; Cl, 6.03%.

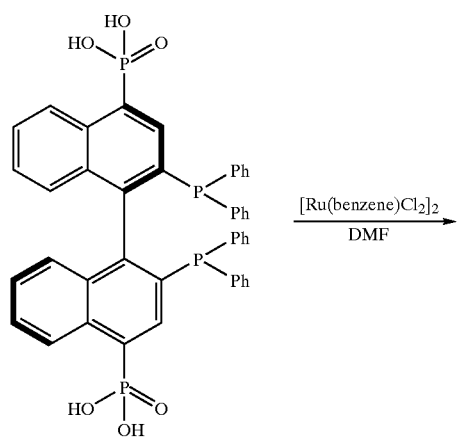

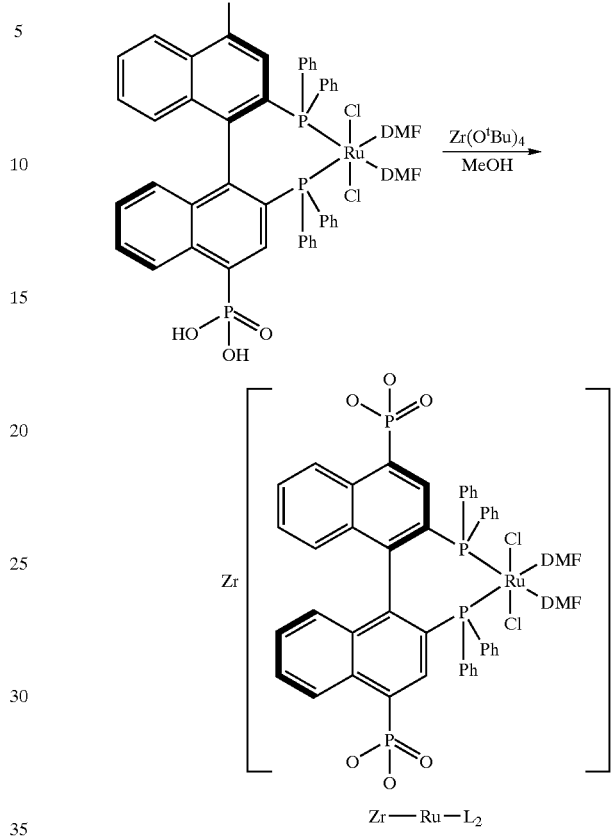

5. Typical Procedures for Asymmetric Hydrogenation of β-Keto Ester.

Solid catalyst (6.0 mg, 5 μmole) was weighed into a test tube (reaction flask) in drybox, and to this tube was added methyl acetoacetate (55 μL, 0.5 mmol) and anhydrous methanol (1 mL) under argon. The test tube was quickly transferred inside a stainless steel autoclave, and sealed. After purging with hydrogen for 6 times, final H$_2$ pressure was adjusted to 1400 psi or 700 psi. 20 hrs later, H$_2$ pressure was released and methanol was removed in vacuo. The hydrogenated product was extracted with diethyl ether and passed through a mini silica-gel column to get rid of residual solid. The conversions were assessed based on the integration of $^1$H NMR peaks of the products and starting materials, while the e.e. values were determined using GC.

For the catalyst re-use experiments, the reaction mixture was centrifuged for 30 minutes and the liquid layer was siphoned out. The residual solid was washed with anhydrous degassed methanol twice. The β-keto ester substrates and methanol were then charged for another round of hydrogenation reaction.

Racemic samples were prepared using rac-BINAP as ligand, and were used to establish GC conditions. The absolute configurations of enantio-enriched products from the present experiments were assigned on GC to be same as those samples obtained from R-BINAP catalyzed reactions.

Methyl 3-hydroxybutyrate: $^1$H NMR (CDCl$_3$): δ 4.12 (m, $^3J_{H\text{-}H}$=6.2 Hz, $^3J_{H\text{-}H}$=1.0 Hz, 1H), 3.62 (s, 3H), 3.35(br, 1H), 2.39(m, $^3J_{H\text{-}H}$=2.8 Hz, $^3J_{H\text{-}H}$=0.5 Hz, 2H), 1.14 (d, $^3J_{H\text{-}H}$=6.2 Hz, 3H). GC (Supelco γ-Dex 225 30m×0.25 mm×0.25 μm, injector: 220° C., Column: 70° C. (iso), Detector: 250° C., carrier gas: He 1.0 mL/min): t$_1$=24.7 min; t$_2$=26.8 min.

Iso-propyl 3-hydroxybutyrate: $^1$H NMR (CDCl$_3$): δ 4.97 (m, $^3J_{H-H}$=6.3 Hz, 1H), 4.12(m, $^3J_{H-H}$=6.3 Hz, 1H), 3.30(br, 1H), 2.34(m, 2H), 1.18 (d, $^3J_{H-H}$=6.3 Hz, 6H), 1.15 (d, $^3J_{H-H}$=6.3 Hz, 3H). GC (Supelco γ-Dex 225 30 m×0.25 mm×0.25 μm, injector: 220° C., Column: 65° C. (iso), Detector: 250° C., carrier gas: He 1.2 mL/min): $t_1$=32.2 min; $t_2$=33.4 min.

Tert-butyl 3-hydroxybutyrate: $^1$H NMR (CDCl$_3$): δ 4.97 (m, $^3J_{H-H}$=6.3 Hz, $^3J_{H-H}$=8.6 Hz, $^3J_{H-H}$=3.9 Hz, 1H), 3.20 (br, 1H), 2.34 (m, $^2J_{H-H}$=16.4 Hz, $^3J_{H-H}$=8.6 Hz, $^3J_{H-H}$=3.9 Hz, 2H), 1.44 (s, 9H), 1.17 (d, $^3J_{H-H}$=6.3 Hz, 3H). GC (Supelco γ-Dex 225 30 m×0.25 mm×0.25 μm, injector: 220° C., Column: 65° C. (iso), Detector: 250° C., carrier gas: He 1.2 mL/min): $t_1$=34.8 min; $t_2$=35.8 min.

Methyl 2,2-dimethyl-3-hydroxybutyrate: $^1$H NMR (CDCl$_3$): δ 3.82 (m, $^3J_{H-H}$=6.7 Hz, 1H), 3.64 (s, 3H), 2.84(br, 1H), 1.11 (s, 6H), 1.07 (d, $^3J_{H-H}$=6.7 Hz, 3H). GC (Supelco γ-Dex 225 30 m×0.25 mm×0.25 μm, injector: 220° C., Column: from 60° C. to 120° C. programmed at 1.5° C./min, Detector: 250° C., carrier gas: He 1.2 mL/min): $t_1$=32.2 min; $t_2$=33.4 min.

Ethyl 3-hydroxyvalerate: $^1$H NMR (CDCl$_3$): δ 4.16 (m, $^3J_{H-H}$=7.1 Hz, 2H), 3.92 (m, $^3J_{H-H}$=6.6 Hz, $^3J_{H-H}$=9.0 Hz, $^3J_{H-H}$=3.1 Hz, 1H), 2.44 (m, $^2J_{H-H}$=16.4 Hz, $^3J_{H-H}$=9.0 Hz, $^3J_{H-H}$=3.1 Hz, 2H), 1.51 (m, $^3J_{H-H}$=6.6 Hz, $^3J_{H-H}$=7.4 Hz, 2H), 1.26 (t, $^3J_{H-H}$=7.1 Hz, 3H), 0.94 (t, $^3J_{H-H}$=7.4 Hz, 3H). GC: (Supelco γ-Dex 225 30 m×0.25 mm×0.25 μm, injector: 220° C., Column: 75° C. (iso), Detector: 250° C., carrier gas: He 1.0 mL/min): $t_1$=29.1 min; $t_2$=29.6 min.

Ethyl 3-hydroxy-3-phenyl-propionate: $^1$H NMR (CDCl$_3$): δ 7.29 (m, 5H), 5.08 (m, $^3J_{H-H}$=8.6 Hz, $^3J_{H-H}$=3.1 Hz,1H), 4.12 (m, $^3J_{H-H}$=7.1 Hz, 2H), 3.61(br, 1H), 2.68 (m, $^2J_{H-H}$=16.2 Hz, $^3J_{H-H}$=9.0 Hz, $^3J_{H-H}$=3.9 Hz, 2H), 1.21 (t, $^3J_{H-H}$=7.1 Hz, 3H). GC (Supelco γ-Dex 225 30 m×0.25 mm×0.25 μm, injector: 220° C., Column: from 70° C. to 180° C. programmed at 1.5° C./min, Detector: 250° C., carrier gas: He 1.0 mL/min): $t_1$=60.5 min; $t_2$=60.8 min.

Example 2

Treatment of (R)-2,2'-bis(diphenylphosphino)-1,1'-binaphthyl-4,4'-bis(phosphonic acid), L$_2$—H$_4$, with [Ru(benzene)Cl$_2$]$_2$ followed by (R,R)-DPEN afforded the phosphonic acid-substituted Ru-BINAP-DPEN intermediate, which was directly reacted with Zr(O$^t$Bu)$_4$ under reflux conditions to give chiral porous Zr phosphonate of the approximate formula Zr[Ru(L$_2$)(DPEN)Cl$_2$].4H$_2$O (Zr—Ru—L$_2$-DPEN). The solid precatalyst Zr—Ru—L$_1$-DPEN with a 6,6'-disubstituted BINAP was similarly prepared, and also has an approximate formula of Zr[Ru(L$_1$)(DPEN) Cl$_2$].4H$_2$O. These chiral porous Zr phosphonates have been characterized with a variety of techniques including thermal gravimetric analysis (TGA), adsorption isotherms, x-ray diffraction (XRD), scanning electron micrography (SEM), infrared spectroscopy (IR), and microanalysis. (FIGS. 12–22) The scheme for production is shown below.

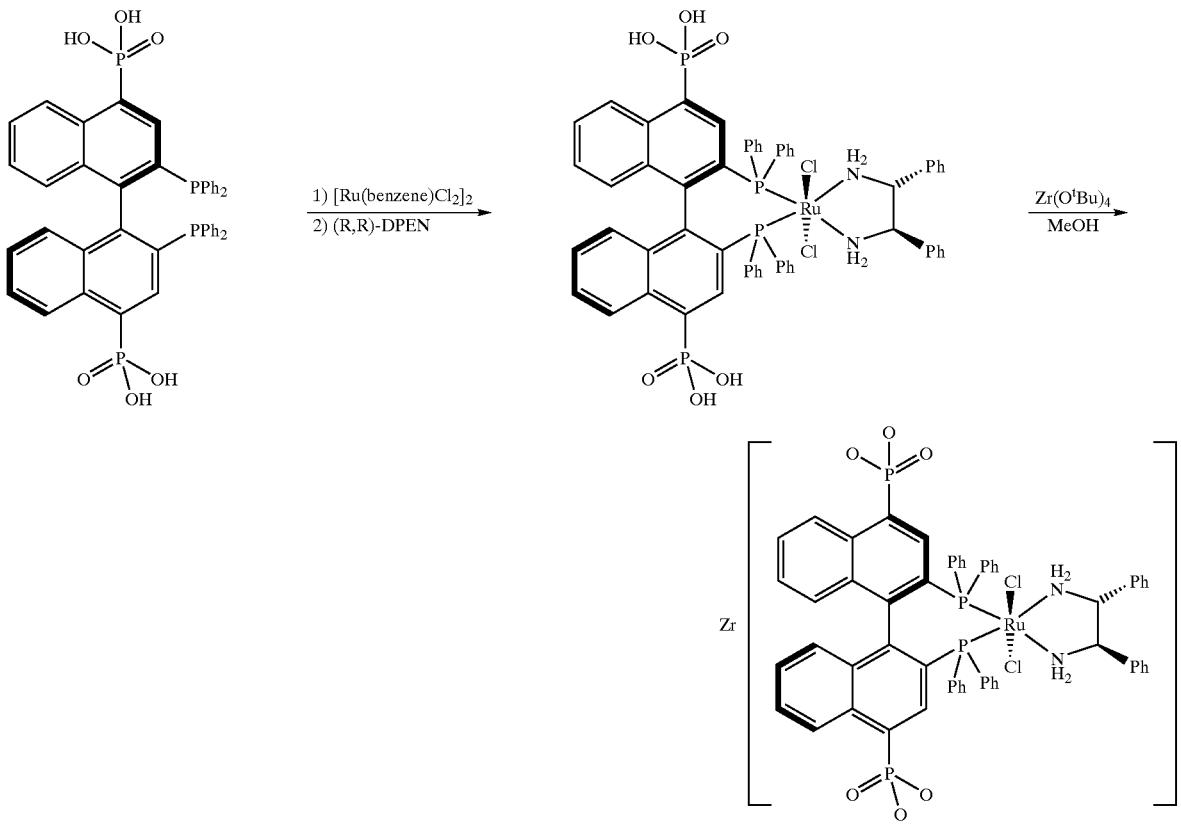

Scheme 2

III

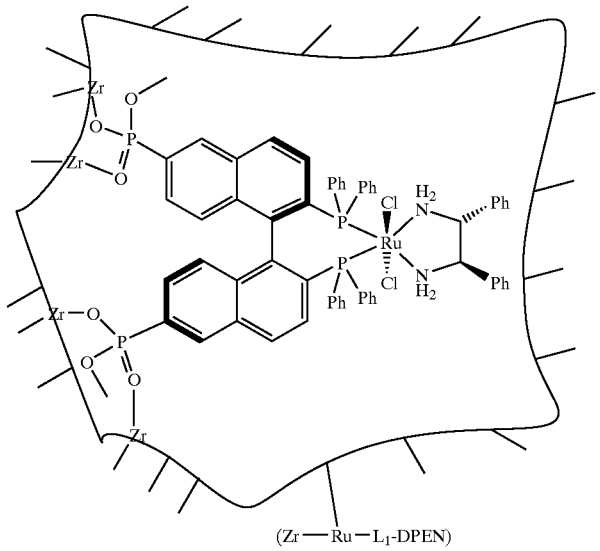

(Zr—Ru—L₁-DPEN)

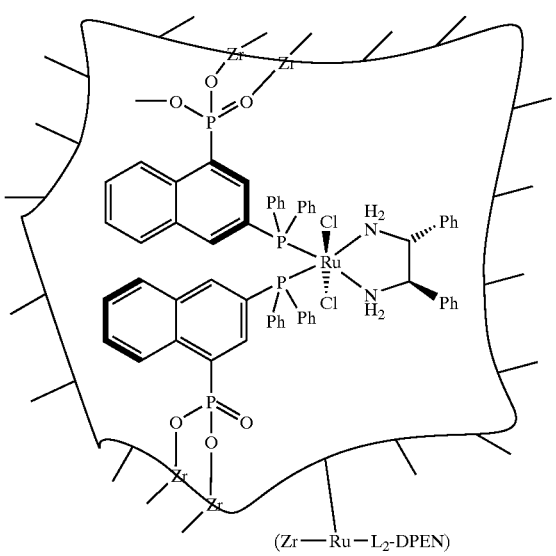

(Zr—Ru—L₂-DPEN)

Figure 12:
FIG. 12 is a scanning electron micrograph (SEM) of Zr—Ru—$L_2$-DPEN as obtained by the experimental procedures described in Example 2.
Figure 13:
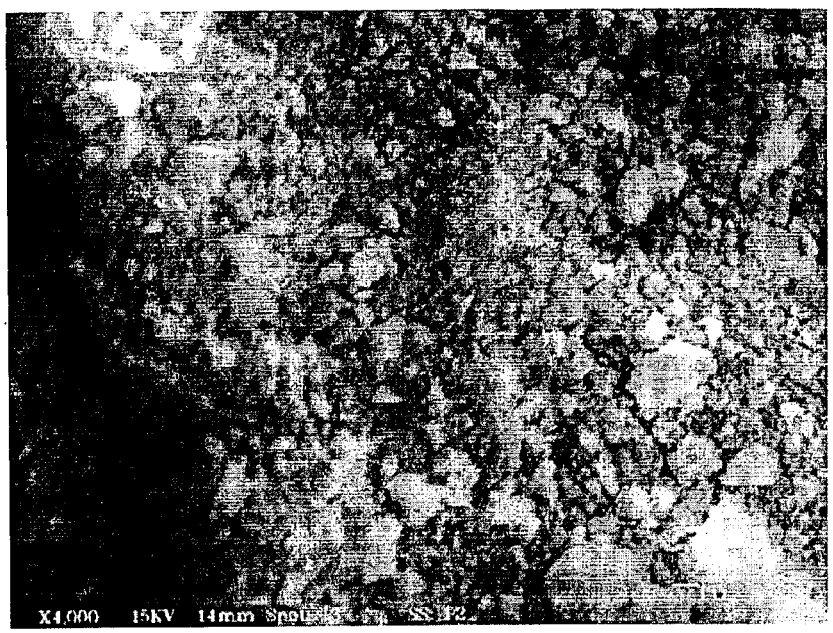
FIG. 13 is a scanning electron micrograph (SEM) of Zr—Ru—$L_1$-DPEN as obtained by the experimental procedures described in Example 2.
Figure 14:
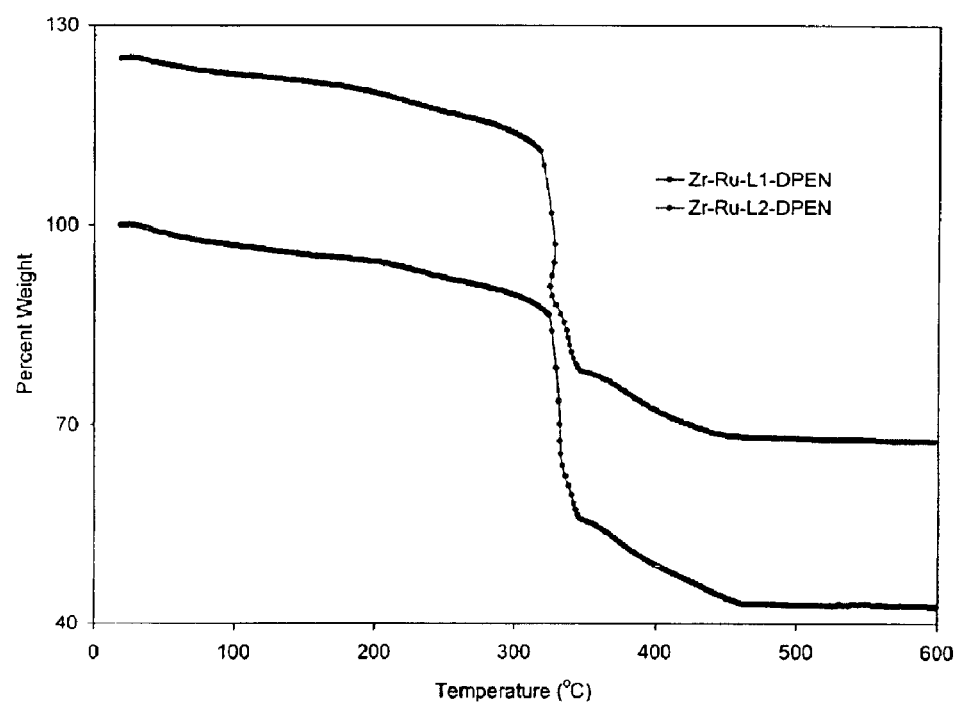
FIG. 14 is a graphical representation of TGA curves of Zr—Ru—$L_2$-DPEN and Zr—Ru—$L_1$-DPEN as obtained by the experimental procedures described in Example 2.
Figure 15:
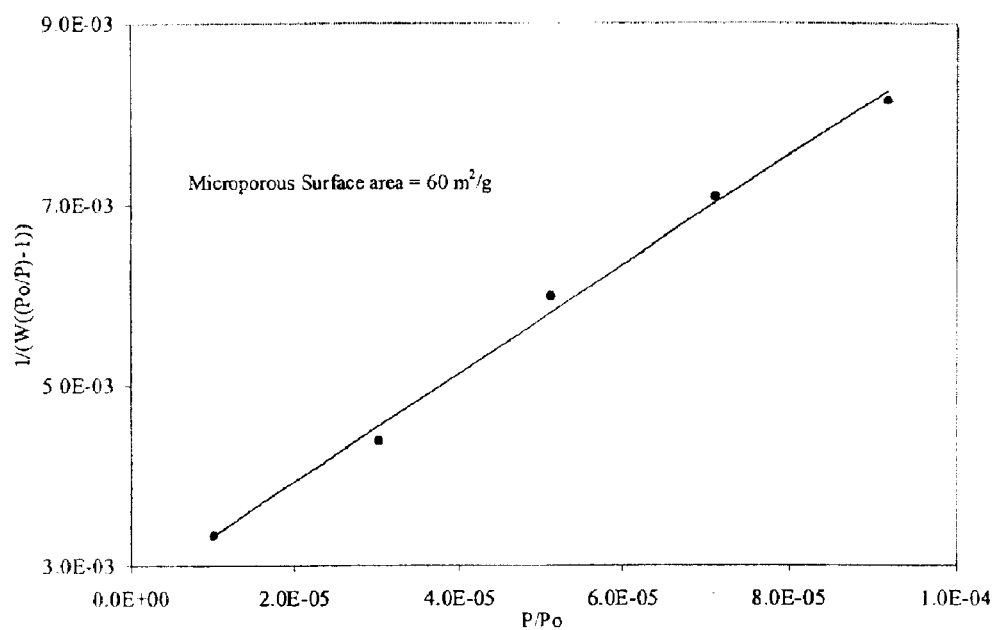
FIG. 15 is a graphical representation of microporous BET plot for Zr—Ru—$L_2$-DPEN as obtained by the experimental procedures described in Example 2.
Figure 16:
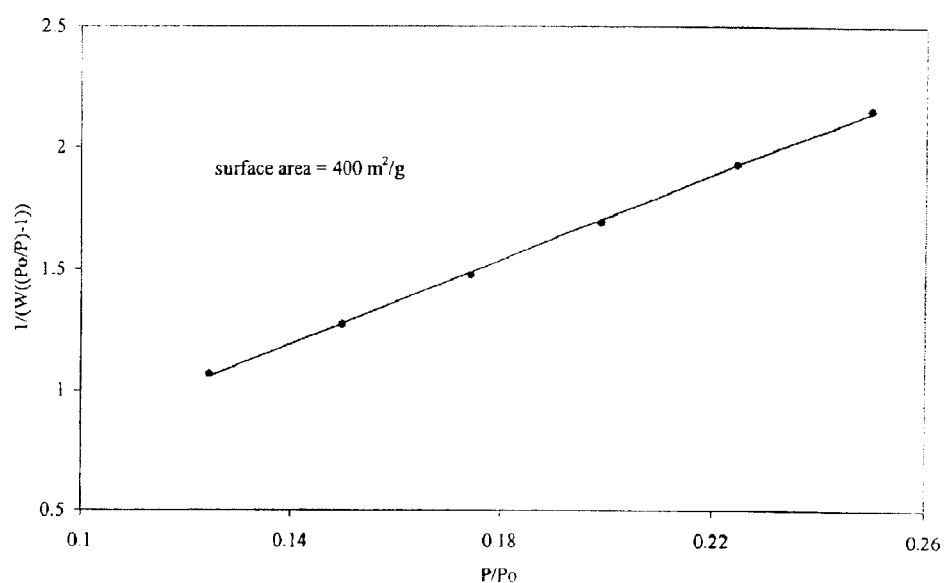
FIG. 16 is a graphical representation of BET plot for Zr—Ru—$L_1$-DPEN as obtained by the experimental procedures described in Example 2.
Figure 17:
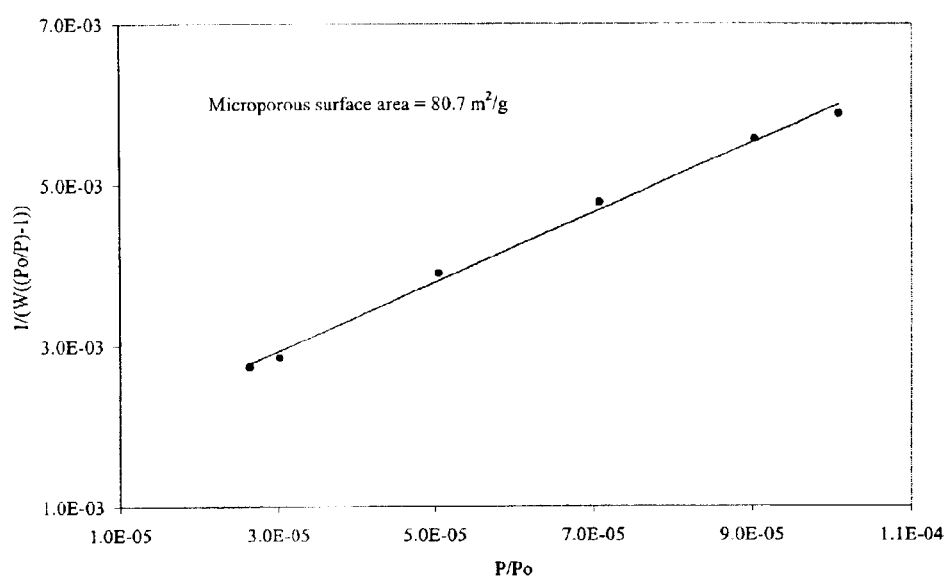
FIG. 17 is a graphical representation of microporous BET plot for Zr—Ru—$L_1$-DPEN as obtained by the experimental procedures described in Example 2.
Figure 18:
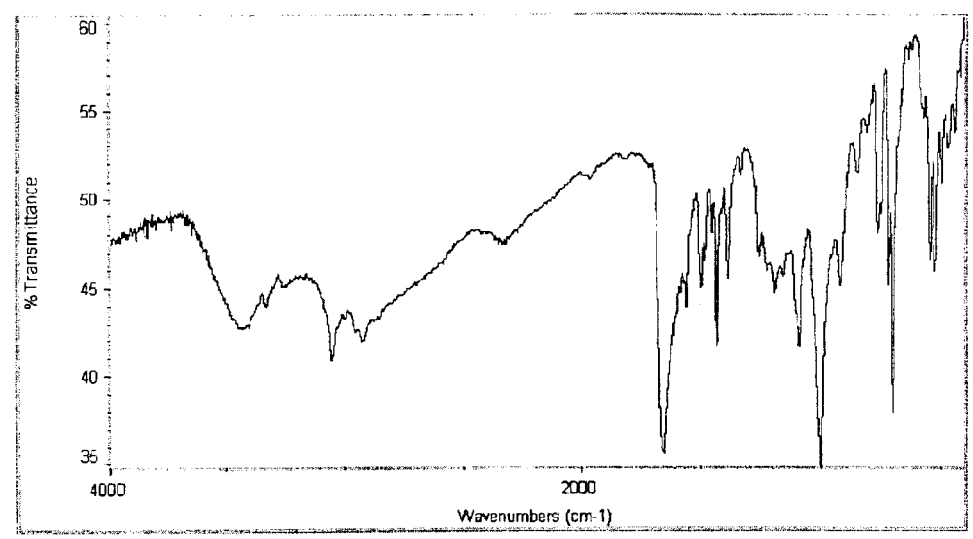
FIG. 18 is a graphical representation of a FT-IR spectrum of Ru($L_2$—$H_4$)(DPEN)Cl$_2$ as obtained by the experimental procedures described in Example 2.
Figure 19:
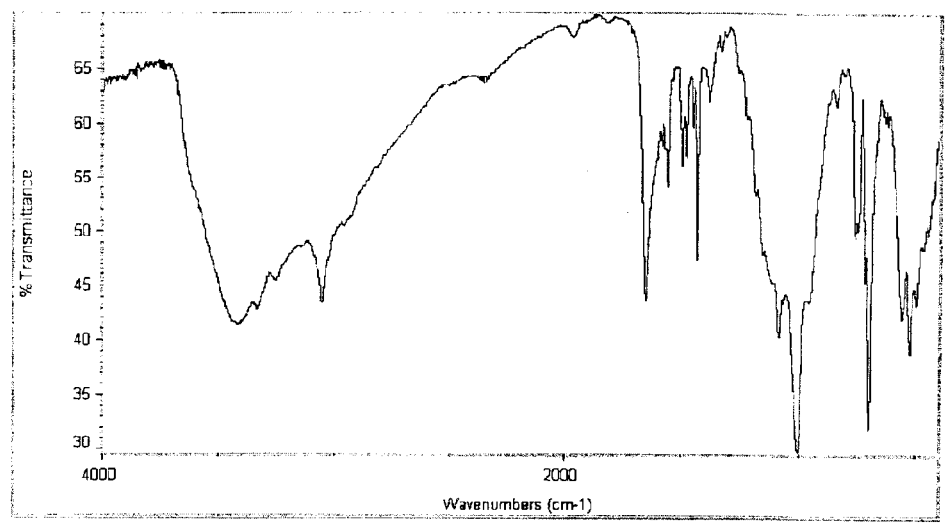
FIG. 19 is a graphical representation of a FT-IR spectrum of Zr—Ru—$L_2$-DPEN as obtained by the experimental procedures described in Example 2.
Figure 20:
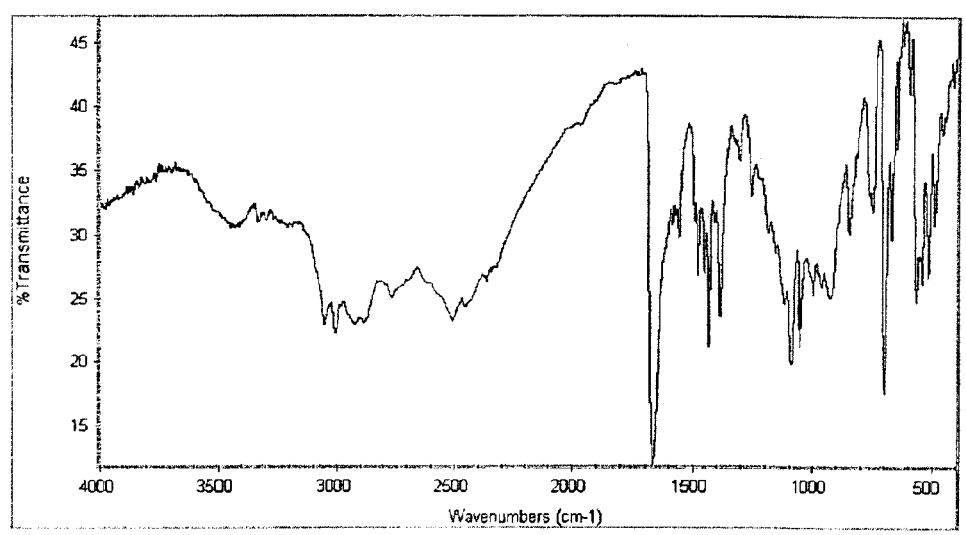
FIG. 20 is a graphical representation of a FT-IR spectrum of Ru($L_1$—$H_4$)(DPEN)Cl$_2$ as obtained by the experimental procedures described in Example 2.
Figure 21:
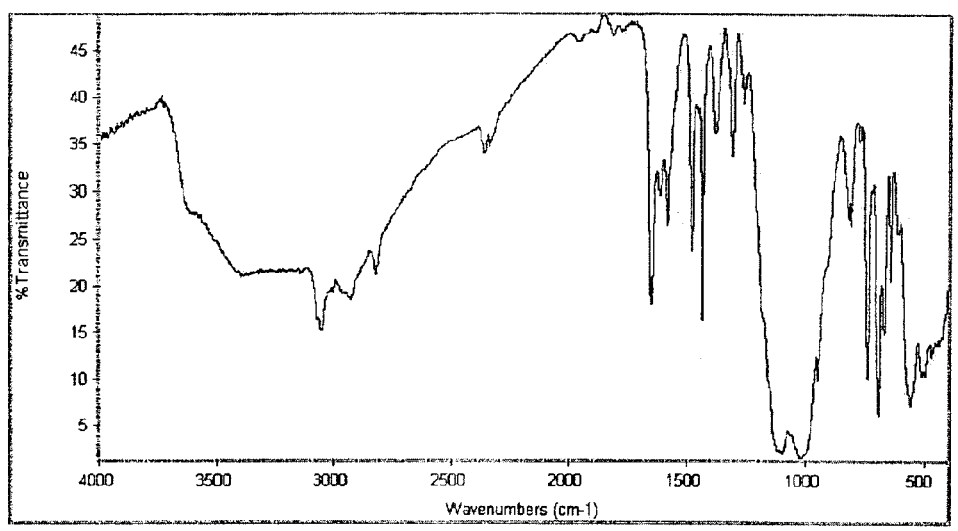
FIG. 21 is a graphical representation of a FT-IR spectrum of Zr—Ru—$L_1$-DPEN as obtained by the experimental procedures described in Example 2.
Figure 22:
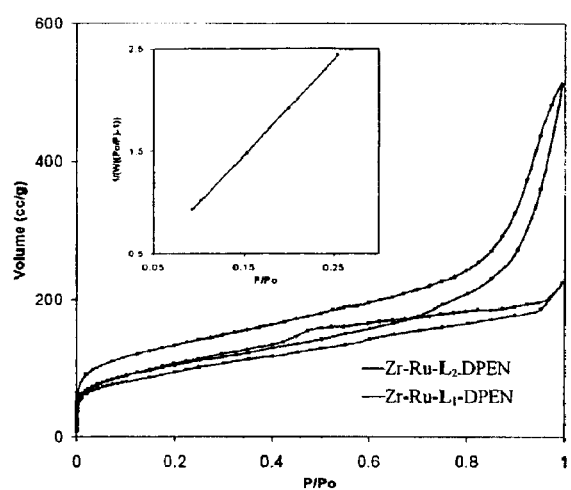
FIG. 22 is a graphical representation of $N_2$ adsorption isotherms for Zr—Ru—$L_1$-DPEN and Zr—Ru—$L_2$-DPEN at 77K. The experimental procedures are described in Example 2. The inset shows BET plot for Zr—Ru—$L_2$-DPEN.
Figure 23:
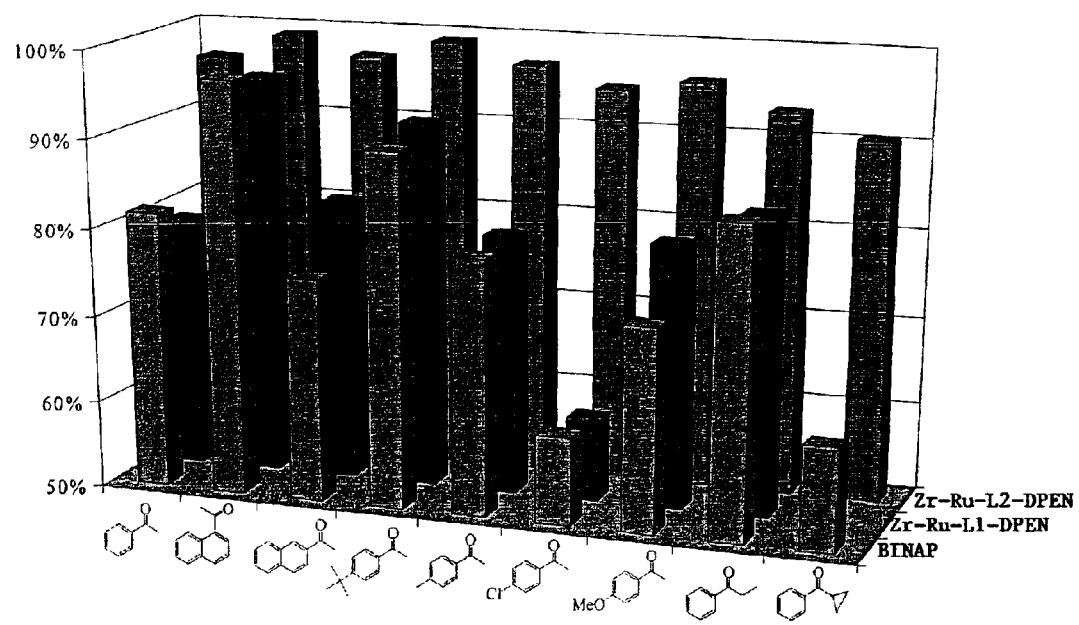
FIG. 23 is a graphical representation of a comparison between a Ru-BINAP-based-homogeneous catalyst and Zr—Ru—$L_1$-DPEN and Zr—Ru—$L_2$-DPEN according to Example 2.

TGA results (FIG. 14) indicated that Zr—Ru—L₂-DPEN and Zr—Ru—L₁-DPEN lost 5.1% and 5.4% of their weights by 200° C. respectively, corresponding to the removal of all the water molecules (expected 5.42%). These formulations are supported by the microanalysis results. The IR spectra (FIGS. 18–21) exhibit strong and broad peaks at 950–1150 cm$^{-1}$ for the P—O stretches, suggesting the formation of Zr-phosphonate bonds. The IR spectra also exhibit intense and broad O—H stretching vibrations at ~3350 cm$^{-1}$, consistent with the presence of H₂O solvates. Nitrogen adsorption measurements (FIG. 22) indicate that both Zr—Ru—L₂-DPEN and Zr—Ru—L₁-DPEN are highly porous with rather wide pore size distributions. Zr—Ru—L₂-DPEN exhibits a total BET surface area of 328 m²/g with a microporous surface area of 60 m²/g (FIG. 15) and a pore volume of 0.65 cm³/g (by BJH method). Zr—Ru—L₁-DPEN) exhibits a total BET surface area of 400 m²/g (FIG. 16) with a microporous surface area of 81 m²/g (FIG. 17) and a pore volume of 0.98 cm³/g (by BJH method). SEM images show that both solids are composed of submicrometer particles, while powder x-ray diffraction (PXRD) indicate that both solids are amorphous. (FIG. 12–13). With the built-in Ru-BINAP-DPEN moieties, porous solids of Zr—Ru—L₁-DPEN and Zr—Ru—L₂-DPEN exhibited exceptionally high activity and enantioselectivity in hydrogenation of aromatic ketones. Acetophenone was hydrogenated to 1-phenylethanol with complete conversion and 96.3% e.e. in isopropanol with 0.1 mol % loading of Zr—Ru—L₂-DPEN solid. This level of enantioselectivity is significantly higher than that observed for the parent Ru-BINAP-DPEN homogeneous catalyst which typically gives ~80% e.e. for the hydrogenation of acetophenone under similar conditions. In comparison, the Zr—Ru—L₁-DPEN solid gives 79.0% e.e. for the hydrogenation of acetophenone under the same conditions. As Table 2 and FIG. 23 show, the Zr—Ru—L₂-DPEN solid has also been used to catalyze a series of other aromatic ketones with uniformly and remarkably high e.e.'s of 90.6–99.2% and complete conversions. Although the Zr—Ru—L₁-DPEN solid is also highly active for the hydrogenation of aromatic ketones, the enantioselectivity of Zr—Ru—L₁-DPEN is modest and similar to that of parent Ru-BINAP-DPEN homogeneous catalyst. Aromatic ketones can also be hydrogenated with much lower catalyst loading. For example, with only 0.02 mol % solid loading of Zr—Ru—L₂-DPEN, 1-acetonaphthone can be hydrogenated with complete conversion and 98.9% e.e. in 20 h. When the solid loading was decreased to 0.005 mol %, it took longer reaction time (40 h) for the hydrogenation of 1-acetonaphthone to complete (98.6% e.e). The TOF is calculated to be ~500 h$^{-1}$ at complete conversion and ~700 h$^{-1}$ at 70% conversion.

TABLE 2

Heterogeneous Asymmetric Hydrogenation of Aromatic Ketones[a]

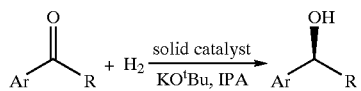

| Substrate | Solid Loading | KO$^t$Bu | Zr—Ru—L₂-DPEN e.e. % | Zr—Ru—L₁-DPEN e.e. % |
|---|---|---|---|---|
| Ar = Ph, R = Me | 0.1% | 1% | 96.3 (97.1)[b] | 79.0 (81.3)[b] |
| Ar = 2-naphthyl, R = Me | 0.1% | 1% | 97.1 | 82.1 |
| Ar = 4'-$^t$Bu—Ph, R = Me | 0.1% | 1% | 99.2 | 91.5 |
| Ar = 4'-MeO—Ph, R = Me | 0.1% | 1% | 96.0 | 79.9 |

TABLE 2-continued

Heterogeneous Asymmetric Hydrogenation of Aromatic Ketones[a]

$$\underset{Ar}{\overset{O}{\underset{\|}{C}}}R + H_2 \xrightarrow[KO^tBu, IPA]{\text{solid catalyst}} \underset{Ar}{\overset{OH}{\underset{\|}{C}}}R$$

| Substrate | Solid Loading | KO$^t$Bu | Zr—Ru—L$_2$-DPEN e.e. % | Zr—Ru—L$_1$-DPEN e.e. % |
|---|---|---|---|---|
| Ar = 4'-Cl—Ph, R = Me | 0.1% | 1% | 94.9 | 59.3 |
| Ar = 4'-Me—Ph, R = Me | 0.1% | 1% | 97.0 | 79.5 |
| Ar = Ph, R = Et | 0.1% | 1% | 93.1 | 83.9 |
| Ar = Ph, R = cyclo-Pr | 0.1% | 1% | 90.6 | — |
| Ar = 1-naphthyl, R = Me | 0.1% | 1% | 99.2 | 95.8 |
| | 0.02% | 0.4% | 98.9 | |
| | 0.005% | 0.02% | 98.8(70%)[c] | |
| | 0.005% | 0.02% | 98.6[d] | |

[a]All of the reactions were carried out in 20 h and the e.e. values were determined by GC on a Supelco β-Dex 120 column. The absolute configurations of the products are identical to those obtained by the Ru—(R)-BINAP-(R,R)-DPEN catalyst. All the conversions were >99% as judged by the integrations of $^1$H NMR spectra.
[b]homogeneous reactions.
[c]70% conversion.
[d]40 h reaction time.

Both the Zr—Ru—L$_2$-DPEN and the Zr—Ru—L$_1$-DPEN systems may be re-used for asymmetric hydrogenation of 1-acetonaphthone without the deterioration of enantioselectivity. As shown in Table 3, the Zr—Ru—L$_2$-DPEN system was used for eight cycles of hydrogenation without any loss of enantioselectivity. The activity did not decrease for the first six runs, but began to drop at the seventh run. This loss of activity may not reflect the intrinsic instability of the Zr—Ru—L$_2$-DPEN solid catalyst. The catalyst recycling and reuse experiments were conducted without rigorous exclusion of air, and the oxygen sensitivity of the ruthenium hydride complexes may have contributed to the loss of activity after multiple runs. The Zr—Ru—L$_1$-DPEN system has also been reused for hydrogenation of 1-acetonaphthone for three times with complete conversions and enantioselectivity of 96.3%, 95.7%, and 94.7%, respectively.

TABLE 3

Recycling and reuse of Zr—Ru—L$_2$—DPEN solid catalyst for hydrogenation of 1-acetonaphthone[a]

| | run | | | | | | | |
|---|---|---|---|---|---|---|---|---|
| | 1 | 2 | 3 | 4 | 5 | 6 | 7 | 8 |
| e.e. % | 99.0 | 99.0 | 99.1 | 99.0 | 99.0 | 99.2 | 99.1 | 99.0 |
| conversion % | 100 | 100 | 100 | 100 | 100 | 100 | 95 | 85 |

[a]The reactions were carried out with 0.1 mol % solid loading and 1% KO$^t$Bu under 700 psi H$_2$ pressure for 20 h.

The Zr—Ru—L$_2$-DPEN solid catalyzes heterogeneous asymmetric hydrogenation of aromatic ketones with practically useful, remarkably high activity and enantioselectivity (up to 99.2% e.e.). These solid catalysts can be readily recycled and reused without the loss of activity and enantioselectivity.

Experimental Procedures.

1. Synthesis of Zr—Ru—L$_2$-DPEN.4H$_2$O

A mixture of [Ru(benzene)Cl$_2$]$_2$ (23 mg, 0.046 mmole) and L$_2$—H$_4$ (78 mg, 0.1 mmole) in anhydrous DMF (4 mL) was heated at 10° C. under argon for 30 min and then cooled to 25° C. (R)-DPEN (1,2-diphenylethylenediamine, 21.5 mg, 0.1 mmole) was added under argon. With stirring, DPEN was slowly dissolved in ca. 15 min and the color of solution slowly changed from orange-red to yellow. After stirring at 80° C. for 2hr, all the volatile components were removed under vacuum to give yellow solid. This solid was directly used for the formation of zirconium phosphonate. To the yellow solid intermediate was added anhydrous degassed methanol (15 mL), and after 10 min vigorous stirring, the solid was slowly dissolved in methanol to give yellowish solution. Zirconium tetra(tert-butoxide) (40 μL, 0.1 mmole) was then slowly added, and lots of yellow precipitate formed immediately, this mixture was refluxed overnight. After centrifugation and rinsing with anhydrous methanol for three cycles, the residue was dried under vacuum to give a yellow solid (130 mg, quantitative). This solid is not soluble in common organic solvent. Anal. Calcd for C$_{58}$H$_{54}$Cl$_2$N$_2$O$_{10}$P$_4$RuZr, (Zr—Ru(L$_2$-DPEN.4H$_2$O): C, 52.5; H, 4.10; N, 2.11. Found: C, 51.5; H, 3.89; N, 2.07.

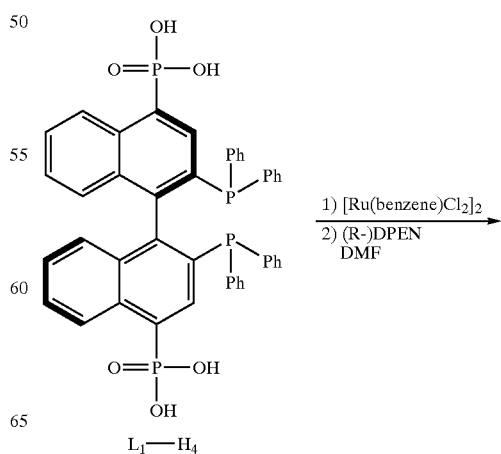

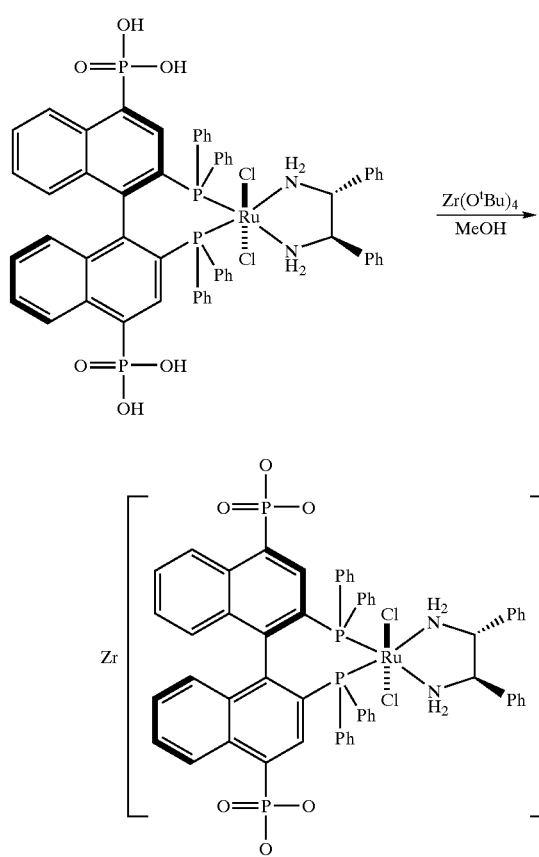

2. Synthesis of Zr—Ru—L₁-DPEN·4H₂O

A mixture of [Ru(benzene)Cl₂]₂ (23 mg, 0.046 mmole) and L₁—H₄ (78 mg, 0.1 mmole) in anhydrous DMF (4 mL) was heated at 100° C. under argon for 30 min and then cooled to 25° C. (R,R)-DPEN (1,2-diphenylethylenediamine, 21.5 mg, 0.1 mmole) was added under argon. With stirring, DPEN was slowly dissolved in ca. 30 min and the color of solution slowly changed from orange-red to yellow. After stirring at 80° C. for 2 hr, all the volatile components were removed under vacuum to give yellow solid. This solid was directly used for the formation of zirconium phosphonate. To the yellow solid intermediate was added anhydrous degassed methanol (15 mL), and after 10 min vigorous stirring, the solid was slowly dissolved in methanol to give yellowish solution. Zirconium tetra(tert-butoxide) (40 μL, 0.1 mmole) was then slowly added, and lots of yellow precipitate formed immediately, this mixture was refluxed overnight. After centrifugation and rinsing with anhydrous methanol for three cycles, the residue was dried under vacuum to give a yellow solid (130 mg, quantitative). This solid is not soluble in common organic solvent. Anal. Calcd for $C_{58}H_{54}Cl_2N_2O_{10}P_4RuZr$, (Zr—Ru—L₂·4H₂O): C, 52.5; H, 4.10; N, 2.11. Found: C, 51.9; H, 3.88; N, 1.61.

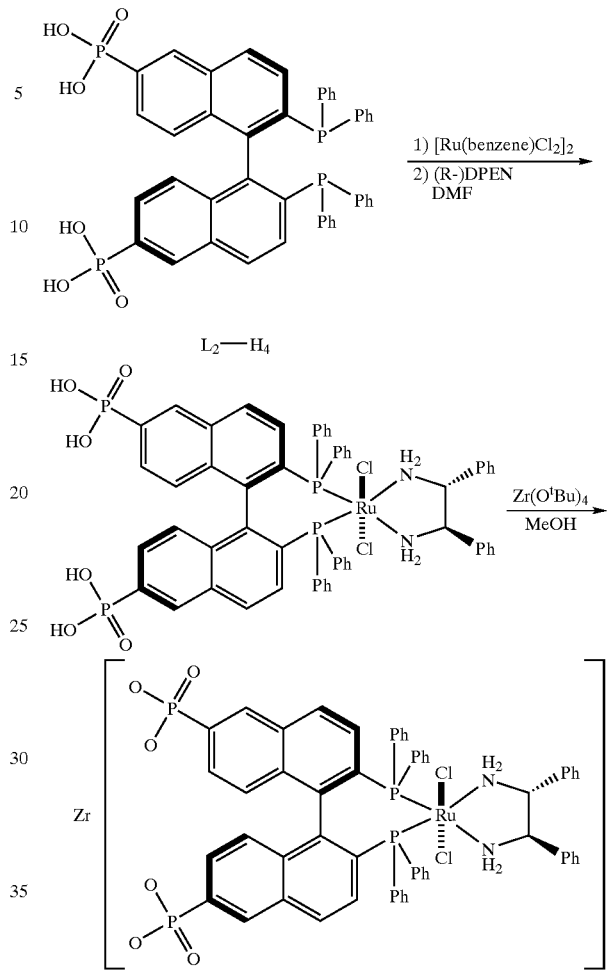

3. Typical Procedure for Asymmetric Hydrogenation of Aromatic Ketones:

Solid catalyst (6.5 mg, 5 μmole calculated on Ru) and potassium tert-butoxide (5.6 mg, 50 μmole) were weighed into a test tube (reaction flask) in a drybox, and then, 1-acetonaphthone (0.85 mL, 5 mmole) and anhydrous isopropanol (2 mL) was added under argon. The test tube was quickly transferred inside a stainless steel a utoclave and sealed. After purging with hydrogen for 6 times, final hydrogen pressure was adjusted to 700 psi. 20 hrs later, hydrogen pressure was released and water (10 mL) and diethyl ether (2 mL) were added. Organic layer was separated out and passed through a mini silica-gel column. An aliquot was analyzed on GC to give conversion and e.e. % value. The absolute configurations of enantio-enriched products from the present experiments were assigned on GC to be same as those samples obtained from R-BINAP catalyzed reactions.

For the catalyst re-use experiment, the reaction mixture was centrifuged for 30 min and the liquid layer was siphoned out. The residual solid was washed with anhydrous degassed isopropanol twice. The ketone substrate and potassium ter-tbutoxide and isopropanol were then charged for another round of hydrogenation reaction.

4. Typical Procedure for Preparing Racemic Products:

In a 220 mL test tube, 1-acetonaphthone (0.85 mL, 5 mmole), sodium borohydride (0.2 g, 5.3 mmole) and ethanol (5 mL) were mixed and stirred overnight, and then quenched with dilute HCl carefully. Diethyl ether (5 mL) was added to this mixture, organic phase was separated out and dried on MgSO$_4$, after removal of solvent, α-(1-naphthyl)ethanol was gotten as colorless oil (0.85 g, 100%).

α-phenylethanol: $^1$H NMR (CDCl$_3$): δ 7.33 (m, 5H), 4.85 (q, $^3J_{H-H}$=6.5 Hz, 1H), 2.62 (br, 1H), 1.46 (d, $^3J_{H-H}$=6.5 Hz, 3H). GC (Supelco β-Dex 120 30 m×0.25 mm×0.25 μm, injector: 220° C., Column: from 100° C. to 140° C. programmed at 1° C./min, Detector: 250° C., carrier gas: He 1.0 mL/min): t$_1$=20.4 min; t$_2$=21.2 min.

α-phenylpropanol: $^1$H NMR (CDCl$_3$): δ 7.31 (m, 5H), 4.55 (t, $^3J_{H-H}$=6.6 Hz, 1H), 1.76 (m, 2H), 0.88 (t, $^3J_{H-H}$=7.4 Hz, 3H). GC (Supelco β-Dex 120 30 m×0.25 mm×0.25 μm, injector: 220° C., Column: from 100° C. to 140° C. programmed at 1° C./min, Detector: 250° C., carrier gas: He 1.0 mL/min): t$_1$=28.6 min; t$_2$=29.3 min.

α-(4-methylphenyl)ethanol: $^1$H NMR (CDCl$_3$): δ 7.23 (d, $^3J_{H-H}$=8.0 Hz, 2H), 7.13 (d, $^3J_{H-H}$=8.0 Hz, 2H), 4.82 (q, $^3J_{H-H}$=6.3 Hz, 1H), 2.32 (s, 3H), 1.45 (d, $^3J_{H-H}$=6.3 Hz, 3H). GC (Supelco β-Dex 120 30 m×0.25 mm×0.25 μm, injector: 220° C., Column: from 100° C. to 140° C. programmed at 1° C./min, Detector: 250° C., carrier gas: He 1.0 mL/min): t$_1$=25.7 min; t$_2$=26.5 min.

α-(1-naphthyl)ethanol: $^1$H NMR (CDCl$_3$): δ 8.05 (m, 1H), 7.84 (m, 1H), 7.74 (d, $^3J_{H-H}$=8.0 Hz, 1H), 7.65 (d, $^3J_{H-H}$=7.0 Hz, 1H), 7.45(m, 3H), 5.59 (q, $^3J_{H-H}$=6.5 Hz, 1H), 1.60 (d, $^3J_{H-H}$=6.5 Hz, 3H). GC (Supelco β-Dex 120 30 m×0.25 mm×0.25 μm, injector: 220° C., Column: from 140° C. to 180° C. programmed at 1° C./min then kept at 180° C. for 20 min, Detector: 250° C., carrier gas: He 1.0 mL/min): t$_1$=38.8 min; t$_2$=39.3 min.

α-(2-naphthyl)ethanol: $^1$H NMR (CDCl$_3$): δ 7.82 (m, 4H), 7.48 (m, 3H), 5.00 (m, $^3J_{H-H}$=6.5 Hz, $^3J_{H-H}$=3.6 Hz, 1H), 2.49 (br, 1H), 1.55 (d, $^3J_{H-H}$=6.5 Hz, 3H). GC (Supelco β-Dex 120 30 m×0.25 mm×0.25 μm, injector: 220° C., Column: from 140° C. to 180° C. programmed at 1° C./min then kept at 180° C. for 20 min, Detector: 250° C., carrier gas: He 1.0 mL/min): t$_1$=38.1 min; t$_2$=38.4 min.

α-(4-tertbutylphenyl)ethanol: $^1$H NMR (CDCl$_3$): δ 7.35 (m, 4H), 4.88 (q, $^3J_{H-H}$=6.5 Hz, 1H), 1.71 (br, 1H), 1.50 (d, $^3J_{H-H}$=6.5 Hz, 3H), 1.32(s, 9H). GC (Supelco β-Dex 120 30 m×0.25 mm×0.25 μm, injector: 220° C., Column: from 110° C. to 150° C. programmed at 1° C./min then kept at 180° C.for 20 min, Detector: 250° C., carrier gas: He 1.0 mL/min): t$_1$=38.7 min; t$_2$=39.1 min.

α-(4-methoxyphenyl)ethanol: $^1$H NMR (CDCl$_3$): δ 7.24 (d, $^3J_{H-H}$=8.4 Hz, 2H), 6.83 (d, $^3J_{H-H}$=8.4 Hz, 2H), 4.77 (q, $^3J_{H-H}$=6.6 Hz, 1H), 3.76 (s, 3H), 2.57 (br, 1H), 1.42 (d, $^3J_{H-H}$=6.6 Hz, 3H). GC (Supelco β-Dex 120 30 m×0.25 mm×0.25 μm, injector: 220° C., Column: from 130° C. to 170° C. programmed at 1° C./min, Detector: 250° C. , carrier gas: He 1.0 mL/min): t$_1$=20.4 min; t$_2$=20.7 min.

α-(4-chlorophenyl)ethanol: $^1$H NMR (CDCl$_3$): δ 7.27 (m, 5H), 4.80 (q, $^3J_{H-H}$=6.5 Hz, 1H), 2.68 (br, 1H), 1.42 (d, $^3J_{H-H}$=6.5 Hz, 3H). GC (Supelco β-Dex 120 30 m×0.25 mm×0.25 μm, injector: 220° C., Column: from 120° C. to 160° C. programmed at 1° C./min, Detector: 250° C., carrier gas: He 1.0 mL/min): t$_1$=23.6 min; t$_2$=24.4 min.

cyclopropylphenylmethanol: $^1$H NMR (CDCl$_3$): δ 7.40 (m, 5H), 4.02 (d, $^3J_{H-H}$=8.4 Hz, 1H), 2.33 (br, 1H), 1.25 (m, 1H), 0.67 (m, 1H), 0.59 (m, 1H), 0.51 (m, 1H), 0.41 (m, 1H). GC (Supelco β-Dex 120 30 m×0.25 mm×0.25 μm, injector: 220° C. , Column: from 110° C. to 150° C. programmed at 1° C./min, Detector: 250° C. , carrier gas: He 1.0 mL/min): t$_1$=34.1 min; t$_2$=34.5 min.

Other General Experimental Procedures.

Thermogravimetric analysis was performed in air at a scan speed of 4° C./min on a Shimadzu TGA-50 analyzer. Infrared spectra were measured from KBr pellets on a Nicolet Magna-560 FT-IR spectrometer. Microanalysis was performed by the School of Chemical Sciences Microanalytical Laboratory at the University of Illinois at Urbana-Champaign. Scanning electron micrographs were taken on a Cambridge/Leica Stereoscan 440 Scanning electron microscope.

Nitrogen adsorption experiments were performed on a Quantachrome-1C surface area analyzer at liquid nitrogen temperature. All the surface areas were calculated based on multi-point BET plots, while the pore volumes were estimated based on BJH method.

While the preferred aspects of the invention have been disclosed in detail, it will be apparent to one skilled in the art that various changes and modifications can be made without departing from the spirit and scope thereof.

What is claimed is:

1. A method for preparing an asymmetric heterogeneous catalyst comprising preparing a phosphonic acid derivative of a homogeneous asymmetric catalyst and then reacting the phosphonic acid derivative with a metal source to obtain the asymmetric heterogeneous catalyst.

2. The method of claim 1 wherein the metal source is metal alkoxide or metal halide.

3. The method of claim 2 wherein the metal source is metal alkoxide.

4. The method of claim 3 wherein the metal alkoxide is zirconium alkoxide.

5. The method of claim 1 wherein the homogeneous asymmetric catalyst is a metal complex containing a chiral bisphosphine moiety.

6. The method of claim 5 wherein the homogeneous asymmetric catalyst further contains a diamine moiety.

7. The method of claim 5 wherein the metal in the metal complex is ruthenium or rhodium.

8. The method of claim 5 wherein the metal complex comprises Ru-BINAP or Rh-BINAP.

9. A method for preparing a chiral porous metal phosphonate comprising reacting a metal alkoxide with a phosphonic acid derivative of a homogeneous asymmetric catalyst comprising a metal complex containing a chiral bisphosphine moiety.

10. The method of claim 9 wherein the metal alkoxide is zirconium alkoxide.

11. The method of claim 9 wherein the metal complex further contains a diamine moiety and the metal in the metal complex is ruthenium or rhodium.

12. A chiral porous metal phosphonate according to Formula I:

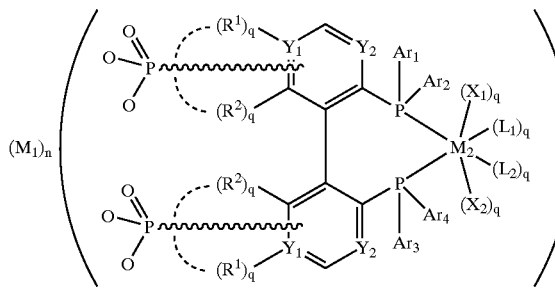

Formula I wherein M1 is a group IV metal, a lanthanide metal, or a first-row transition metal atom other than Ti, n=1–2 and is a quantity such that Formula I retains charge neutrality regardless of the M1 atom used;

M2 is Ru, Rh, Ir, Os, Pt or Pd;

X1 and X2 are covalently or ionically bonded to the M2 center, and each independently represents hydrogen, halogen, an alkoxy group or a carboxyl group;

Ar1, Ar2, Ar3 and Ar4 independently represent a phenyl group substituted with from zero to five substituents selected from straight-chain or branched-chain lower alkyl groups, halogen, or lower alkoxy groups;

L1 and L2 independently represent a coordinated solvent molecule, or donor atoms comprising half of a diamine moiety such that L1 and L2 are joined to give a chelating diamine, or a weakly coordinating ligand comprising an olefin;

Y1 and Y2 independently represent a carbon or nitrogen atom;

R1 and R2 independently represent hydrogen, a lower alkyl group, or a lower alkoxy group, or each pair of R1 and R2 can be the same or different and are bonded such that each R1 and R2 together with the attached ring form a ring selected from a substituted or unsubstituted tetrahydronaphthalene ring, a substituted or unsubstituted naphthalene ring, or a substituted or unsubstituted 1,3-benzodioxole ring, provided, however, that when Y1 is N, R1 is nothing;

represents a bond independently linking the phosphonate groups to the benzene, pyridine, or pyrimidine ring or a ring formed by each of R1 and R2 as defined above, in any of the reasonable positions either directly or through one of the following linkages:

an alkene group, an alkyl group, an aryl group or a styryl group; and each q is independently selected from 0 or 1.

13. A chiral porous metal phosphonate according to claim 12 wherein Ar1=Ar2=Ar3=Ar4 and Ar is an unsubstituted phenyl group.

14. A chiral porous metal phosphonate according to claim 12 wherein Y1 and Y2 are C and each of R1 and R2 are bonded together with the attached benzene ring to form a naphthalene ring.

15. A chiral porous metal phosphonate according to claim 12 wherein M1 is zirconium.

16. A chiral porous metal phosphonate according to claim 12 wherein M2 is ruthenium, rhodium, palladium or iridium.

17. A chiral porous metal phosphonate according to claim 16 wherein M2 is ruthenium.

18. A chiral porous metal phosphonate according to claim 12 wherein Y1 or Y2 is N.

19. A chiral porous metal phosphonate according to claim 12 wherein L1 and L2 are joined together to form a chelating diamine.

20. A chiral porous metal phosphonate according to claim 12 wherein M2 is Rh, L1 and L2 together represent a COD or NBE molecule, X1 represents hydrogen, halogen, an alkoxy group or a carboxyl group wherein q is 1, and for X2, q is 0.

21. An asymmetric heterogeneous catalyst for asymmetric reactions comprising a metal phosphonate framework combined with a highly enantioselective metal complex containing a chiral bisphosphine moiety.

22. The catalyst of claim 21 wherein the metal in the metal phosphonate framework is zirconium.

23. The catalyst of claim 22 wherein the metal complex further contains a diamine moiety and the metal in the metal complex is Ru or Rh.

24. A chiral porous metal phosphonate according to one of the following formulas A–D:

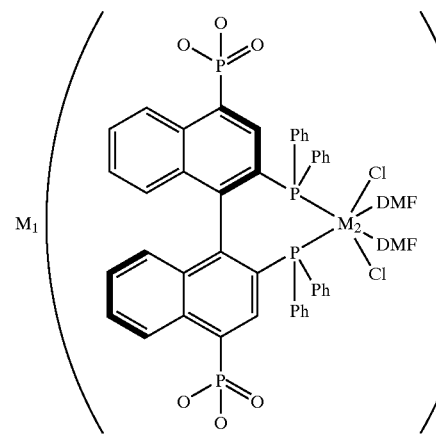

Formula A

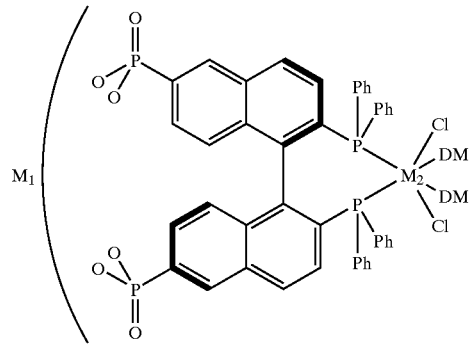

Formula B

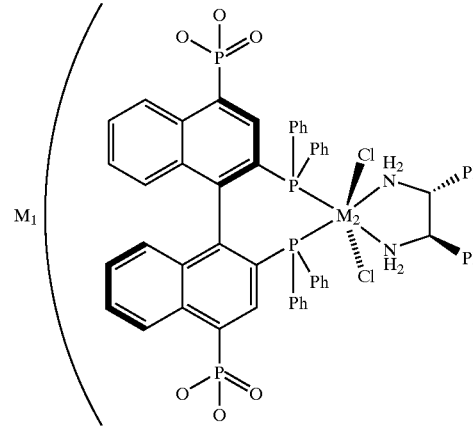

Formula C

-continued

Formula D

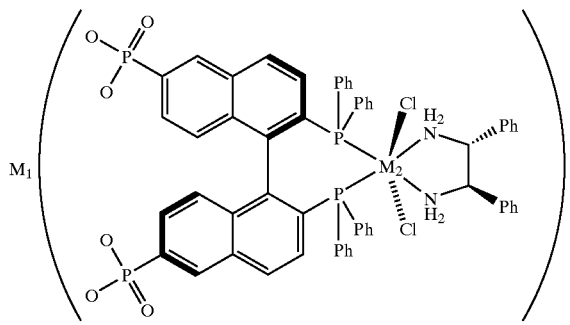

wherein M1 is Zr, Ti or Hf and M2 is Ru or Os.

25. A chiral porous metal phosphonate according to claim 24 wherein M1 is Zr and M2 is Ru.

26. A method for the stereoselective hydrogenation of a substrate capable of forming an asymmetric product by hydrogenation comprising contacting the substrate with a chiral porous metal phosphonate comprising the reaction product of a metal alkoxide and a phosphonic acid derivative of a homogeneous asymmetric catalyst.

27. The method of claim 26 wherein the metal alkoxide is zirconium alkoxide.

28. The method of claim 26 wherein the homogeneous asymmetric catalyst comprises a metal complex containing a bisphosphine moiety.

29. The method of claim 28 wherein the homogeneous asymmetric catalyst further contains a diamine moiety.

30. The method of claim 28 wherein the metal of the metal complex is ruthenium, rhodium, palladium or iridium.

31. The method of claim 30 wherein the metal is ruthenium.

32. A method for the stereoselective hydrogenation of a substrate capable of forming an asymmetric product by hydrogenation comprising contacting the substrate with a chiral porous metal phosphonate according to Formula I:

Formula I

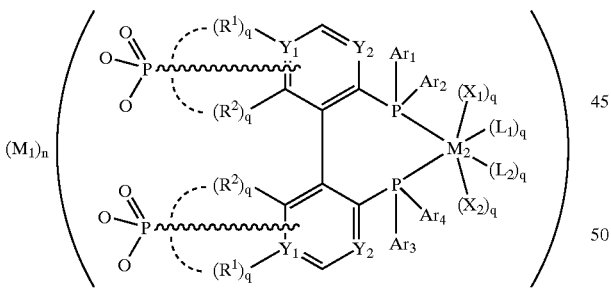

wherein M1 is a group IV metal, a lanthanide metal, or a first-row transition metal atom other than Ti, n=1–2 and is a quantity such that Formula I retains charge neutrality regardless of the M1 atom used;

M2 is Ru, Rh, Ir, Os, Pt or Pd;

X1 and X2 are covalently or ionically bonded to the M2 center, and each independently represents hydrogen, halogen, an alkoxy group or a carboxyl group;

Ar1, Ar2, Ar3 and Ar4 independently represent a phenyl group substituted with from zero to five substituents selected from straight-chain or branched-chain lower alkyl groups, halogen, or lower alkoxy groups;

L1 and L2 independently represent a coordinated solvent molecule, or donor atoms comprising half of a diamine moiety such that L1 and L2 are joined to give a chelating diamine, or a weakly coordinating ligand comprising an olefin;

Y1 and Y2 independently represent a carbon or nitrogen atom;

R1 and R2 independently represent hydrogen, a lower alkyl group, or a lower alkoxy group, or each pair of R1 and R2 can be the same or different and are bonded such that each R1 and R2 together with the attached ring form a ring selected from a substituted or unsubstituted tetrahydronaphthalene ring, a substituted or unsubstituted naphthalene ring, or a substituted or unsubstituted 1,3-benzodioxole ring, provided, however, that when Y1 is N, R1 is nothing;

represents a bond independently linking the phosohonate groups to the benzene, pyridine, or pyrimidine ring or a ring formed by each of R1 and R2 as defined above, in any of the reasonable positions either directly or through one of the following linkages:

an alkene group, an alkyl group, an aryl group or a styryl group; and each q is independently selected from 0 or 1.

33. A method for the stereoselective hydrogenation of a substrate capable of forming an asymmetric product by hydrogenation comprising contacting the substrate with a chiral porous metal phosphonate according to Formula A, Formula B, Formula C or Formula D:

Formula A

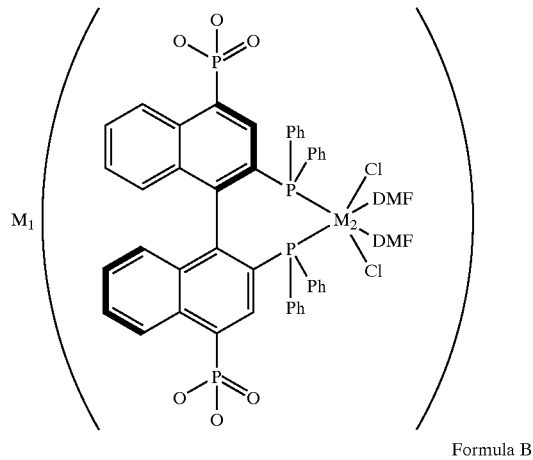

Formula B

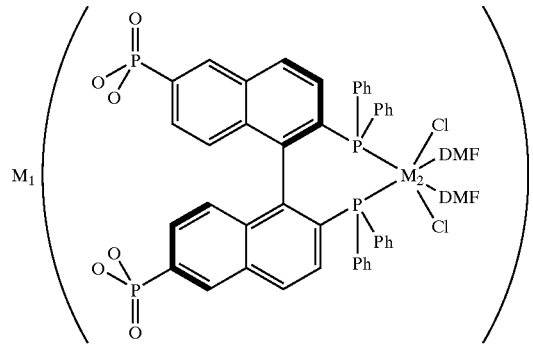

Formula C

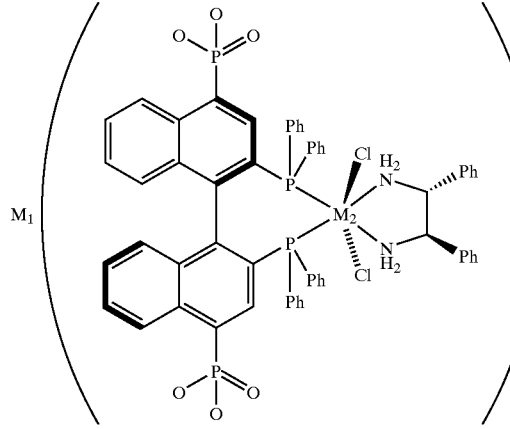

Formula D

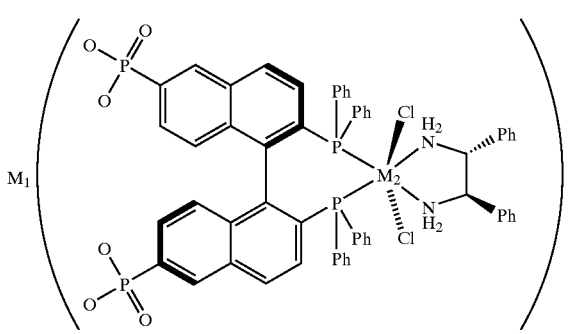

wherein M1 is Zr, Ti or Hf and M2 is Ru or Os.

34. A compound according to one of the following formulas:

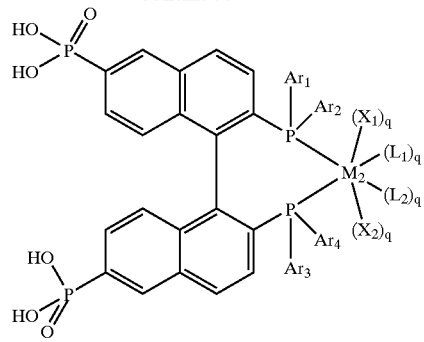

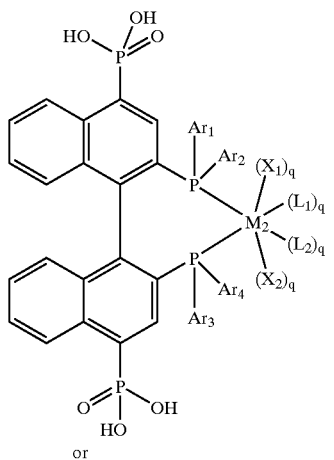

or wherein M2 is Ru, Rh, Ir, Os, Pt or Pd;

X1 and X2 may be covalently or ionically bonded to the M2 center, and each independently represents hydrogen, halogen, an alkoxy group, or a carboxyl group;

Ar1, Ar2, Ar3 and Ar4 independently represent a phenyl group substituted with from zero to five substituents selected from straight-chain or branched-chain lower alkyl groups, halogen, or lower alkoxy groups;

L1 and L2 independently represent a coordinated solvent molecule, or donor atoms comprising half of a diamine moiety such that L1 and L2 are joined to give a chelating diamine; and each q is independently selected from 0 or 1.

35. A compound according to one of the following formulas:

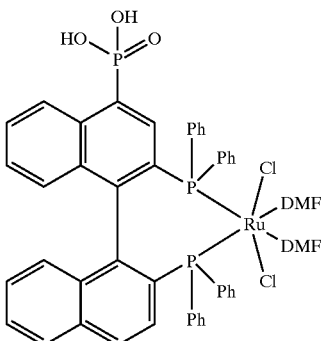

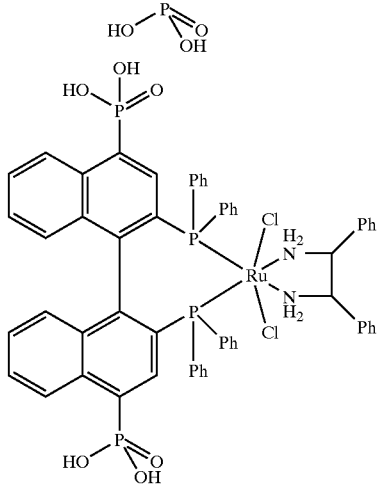

39
-continued
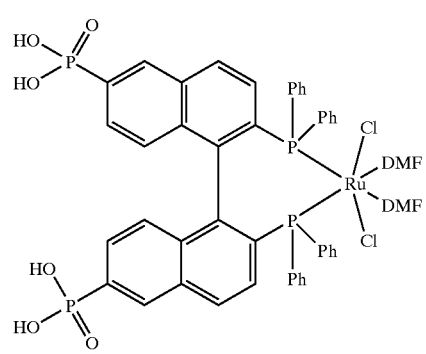
40
-continued
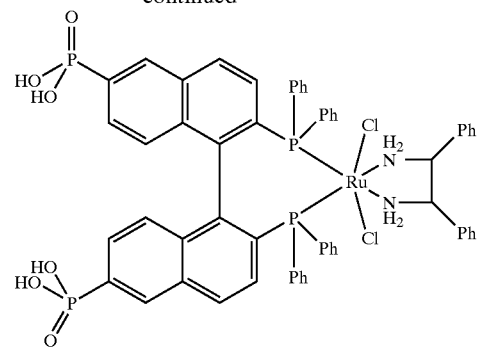
* * * * *